(12) United States Patent
He et al.

(10) Patent No.: US 11,680,086 B2
(45) Date of Patent: Jun. 20, 2023

(54) LIPOPEPTIDE FOR POTENTLY INHIBITING HIV, DERIVATIVE THEREOF, PHARMACEUTICAL COMPOSITION THEREOF AND USE THEREOF

(71) Applicants: Institute of Pathogen Biology, Chinese Academy of Medical Sciences, Beijing (CN); Shanxi Kangbao Biological Product Co., Ltd., Changzhi (CN)

(72) Inventors: Yuxian He, Beijing (CN); Huihui Chong, Beijing (CN); Yuanmei Zhu, Beijing (CN)

(73) Assignees: Shanxi Kangbao Biological Product Co., Ltd., Changzhi (CN); Institute of Pathogen Biology, Chinese Academy of Medical Sciences, Beijing (CN)

(*) Notice: Subject to any disclaimer, the term of this patent is extended or adjusted under 35 U.S.C. 154(b) by 724 days.

(21) Appl. No.: 16/606,525

(22) PCT Filed: Apr. 18, 2017

(86) PCT No.: PCT/CN2017/080860
§ 371 (c)(1),
(2) Date: Oct. 18, 2019

(87) PCT Pub. No.: WO2018/191858
PCT Pub. Date: Oct. 25, 2018

(65) Prior Publication Data
US 2021/0277068 A1    Sep. 9, 2021

(51) Int. Cl.
*A61K 47/02*    (2006.01)
*C07K 14/005*    (2006.01)
*C07K 14/16*    (2006.01)
*A61K 47/54*    (2017.01)
*A61K 38/00*    (2006.01)

(52) U.S. Cl.
CPC .......... *C07K 14/162* (2013.01); *A61K 47/542* (2017.08); *A61K 47/545* (2017.08); *A61K 47/554* (2017.08); *A61K 38/00* (2013.01)

(58) Field of Classification Search
None
See application file for complete search history.

(56) References Cited

U.S. PATENT DOCUMENTS

2009/0298774 A1    12/2009    Jiang et al.

FOREIGN PATENT DOCUMENTS

| CN | 102247590 A | 11/2011 |
|---|---|---|
| CN | 102427829 A | 4/2012 |
| EP | 2291392 B1 | 3/2014 |
| EP | 3 219 732 A1 | 9/2017 |
| JP | 2014-510754 A | 5/2014 |
| WO | WO 2003/029284 A1 | 4/2003 |
| WO | WO 2008/050830 A1 | 5/2008 |
| WO | WO 2010/019717 A2 | 2/2010 |
| WO | WO 2010/113157 A1 | 10/2010 |
| WO | WO 2012/135385 A1 | 10/2012 |
| WO | WO 2013/127300 A1 | 9/2013 |
| WO | WO 2013/150532 A1 | 10/2013 |

OTHER PUBLICATIONS

Ingallinella et al. (PNAS, 2009, p. 5801-5806 in IDS on Oct. 18, 2019).*
Chong et al. (Journal of Virology, Jun. 2017).*
Hollmann et al., Conjugation of Cholesterol to HIV-1 Fusion Inhibitor C34 Increases Peptide-Membrane Interactions Potentiating Its Action. PLoS One. 2013;8(4):e60302. doi: 10.1371/journal.pone.0060302. Epub Apr. 2, 2013.
International Preliminary Report on Patentability for Application No. PCT/CN2017/080860, dated Oct. 31, 2019.
International Search Report and Written Opinion dated Jan. 9, 2018, in connection with PCT/CN2017/080860.
Ashkenazi et al., Sphingopeptides: dihydrosphingosine-based fusion inhibitors against wild-type and enfuvirtide-resistant HIV-1. FASEB J. Nov. 2012;26(11):4628-36. doi: 10.1096/fj.12-215111. Epub Aug. 7, 2012.
Brugger et al., The HIV lipidome: a raft with an unusual composition. Proc Natl Acad Sci U S A. Feb. 21, 2006;103(8):2641-6. Epub Feb. 15, 2006.
Chan et al., Core structure of gp41 from the HIV envelope glycoprotein. Cell. Apr. 18, 1997;89(2):263-73.
Chan et al., Evidence that a prominent cavity in the coiled coil of HIV type 1 gp41 is an attractive drug target. Proc Natl Acad Sci U S A. Dec. 22, 1998;95(26):15613-7.
Chong et al., A Lipopeptide HIV-1/2 Fusion Inhibitor with Highly Potent In Vitro, Ex Vivo, and In Vivo Antiviral Activity. J Virol. May 12, 2017;91(11). pii: e00288-17. doi: 10.1128/JVI.00288-17. Print Jun. 1, 2017.

(Continued)

*Primary Examiner* — Agnieszka Boesen
(74) *Attorney, Agent, or Firm* — Wolf, Greenfield & Sacks, P.C.

(57) ABSTRACT

The present application relates to a lipopeptide for potently inhibiting HIV, a derivative thereof, or a pharmaceutical composition thereof, and use thereof. The lipopeptide is the following a) or b): a) a lipopeptide formed by linking a polypeptide having an antiviral activity to a lipophilic compound linked to the carboxyl-terminus of the polypeptide; or b) a lipopeptide formed by linking a polypeptide having an antiviral activity to a terminal protecting group and a lipophilic compound linked to the carboxyl-terminus of the polypeptide, wherein the terminal protecting group is an amino-terminal protecting group and/or a carboxyl-terminal protecting group, the polypeptide has a sequence of 28 amino acid residues, corresponding to amino acids at positions of 127-154 of the sequence of gp41 from HIV-1 strain HXB2. The anti-HIV activity of the lipopeptide of the present invention is higher than that of T-20 by several thousands of times or even tens of thousands of times, and is also significantly higher than that of the anti-HIV lipopeptides such as C34-Chol, LP-19 and the like.

10 Claims, 8 Drawing Sheets

Specification includes a Sequence Listing.

(56) References Cited

OTHER PUBLICATIONS

Chong et al., Design of a highly potent HIV-1 fusion inhibitor targeting the gp41 pocket. AIDS. Jan. 2, 2015;29(1):13-21. doi: 10.1097/QAD.0000000000000498.

Chong et al., Development of potent and long-acting HIV-1 fusion inhibitors. AIDS. May 15, 2016;30(8):1187-96. doi: 10.1097/QAD.0000000000001073.

Chong et al., Discovery of critical residues for viral entry and inhibition through structural Insight of HIV-1 fusion inhibitor CP621-652. J Biol Chem. Jun. 8, 2012;287(24):20281-9. doi: 10.1074/jbc.M112.354126. Epub Apr. 16, 2012.

Chong et al., Short-peptide fusion inhibitors with high potency against wild-type and enfuvirtide-resistant HIV-1. FASEB J. Mar. 2013;27(3):1203-13. doi: 10.1096/fj.12-222547. Epub Dec. 11, 2012.

Chong et al., The M-T hook structure increases the potency of HIV-1 fusion inhibitor sifuvirtide and overcomes drug resistance. J Antimicrob Chemother. Oct. 2014;69(10):2759-69. doi:10.1093/jac/dku183. Epub Jun. 7, 2014.

Chong et al., The M-T hook structure is critical for design of HIV-1 fusion inhibitors. J Biol Chem. Oct. 5, 2012;287(41):34558-68. doi: 10.1074/jbc.M112.390393. Epub Aug. 9, 2012.

Chong et al., The N-Terminal T-T Motif of a Third-Generation HIV-1 Fusion Inhibitor Is Not Required for Binding Affinity and Antiviral Activity. J Med Chem. Aug. 27, 2015;58(16):6378-88. doi:10.1021/acs.jmedchem.5b00109. Epub Aug. 17, 2015.

Chong et al., Two M-T hook residues greatly improve the antiviral activity and resistance profile of the HIV-1 fusion inhibitor SC29EK. Retrovirology. May 27, 2014;11:40. doi: 10.1186/1742-4690-11-40.

Eckert et al., Mechanisms of viral membrane fusion and its inhibition. Annu Rev Biochem. 2001;70:777-810. Review.

Eggink et al., Inhibition of HIV-1 by fusion inhibitors. Curr Pharm Des. 2010;16(33):3716-28. Review.

Egelhofer et al., Inhibition of human immunodeficiency virus type 1 entry in cells expressing gp41-derived peptides. J Virol. Jan. 2004;78(2):568-75.

Esté et al., HIV entry inhibitors. Lancet. Jul. 7, 2007;370(9581):81-8. Review.

Flexner, HIV drug development: the next 25 years. Nat Rev Drug Discov. Dec. 2007;6(12):959-66. Review.

Franquelim et al., Sifuvirtide screens rigid membrane surfaces. establishment of a correlation between efficacy and membrane domain selectivity among HIV fusion inhibitor peptides. J Am Chem Soc. May 14, 2008;130(19):6215-23. doi: 10.1021/ja711247n. Epub Apr. 15, 2008.

He, Synthesized peptide inhibitors of HIV-1 gp41-dependent membrane fusion. Curr Pharm Des. 2013;19(10):1800-9. Review.

Hildinger et al., Membrane-anchored peptide inhibits human immunodeficiency virus entry. J Virol. Mar. 2001;75(6):3038-42.

Ingallinella et al., Addition of a cholesterol group to an HIV-1 peptide fusion inhibitor dramatically increases its antiviral potency. Proc Natl Acad Sci U S A. Apr. 7, 2009;106(14):5801-6. doi: 10.1073/pnas.0901007106. Epub Mar. 18, 2009.

Liu et al., Peptidic HIV fusion inhibitors targeting envelope glycoprotein transmembrane subunit gp41. Chin Pharm Bull. Nov. 2003;19(11):1201-08.

Matos et al., HIV-1 fusion inhibitor peptides enfuvirtide and T-1249 interact with erythrocyte and lymphocyte membranes. PLoS One. Mar. 23, 2010;5(3):e9830. doi: 10.1371/journal.pone.0009830.

Nishikawa et al., Genbank Submission; NIH/NCBI, Accession No. 2Z2T_D: "Chain D, Fusion Inhibitor Peptide Sc34ek". Last updated Jan. 10, 2013. 1 page.

Ono et al., Plasma membrane rafts play a critical role in HIV-1 assembly and release. Proc Natl Acad Sci U S A. Nov. 20, 2001;98(24):13925-30.

Peisajovich et al., C-terminal octylation rescues an inactive T20 mutant: implications for the mechanism of HIV/SIMIAN immunodeficiency virus-induced membrane fusion. J Biol Chem. Jun. 6, 2003;278(23):21012-7. Epub Mar. 19, 2003.

Veiga et al., HIV fusion inhibitor peptide T-1249 is able to insert or adsorb to lipidic bilayers. Putative correlation with improved efficiency. J Am Chem Soc. Nov. 17, 2004;126(45):14758-63.

Wexler-Cohen et al., Demonstrating the C-terminal boundary of the HIV 1 fusion conformation in a dynamic ongoing fusion process and implication for fusion inhibition. FASEB J. Nov. 2007;21(13):3677-84. Epub Jun. 15, 2007.

Wexler-Cohen et al., Membrane-anchored HIV-1 N-heptad repeat peptides are highly potent cell fusion inhibitors via an altered mode of action. PLoS Pathog. Jul. 2009;5(7):e1000509. doi: 10.1371/journal.ppat.1000509. Epub Jul. 10, 2009.

Wexler-Cohen et al., Virus-cell and cell-cell fusion mediated by the HIV-1 envelope glycoprotein is inhibited by short gp41 N-terminal membrane-anchored peptides lacking the critical pocket domain. FASEB J. Nov. 2010;24(11):4196-202. doi: 10.1096/fj.09-151704. Epub Jul. 6, 2010.

Xiong et al., A Helical Short-Peptide Fusion Inhibitor with Highly Potent Activity against Human Immunodeficiency Virus Type 1 (HIV-1), HIV-2, and Simian Immunodeficiency Virus. J Virol. Dec. 16, 2016;91(1). pii: e01839-16. doi: 10.1128/JVI.01839-16. Print Jan. 1, 2017.

* cited by examiner

| Inhibitor | Sequence structure | Number of amino acids | IC50 (pM) HXB2-cell fusion | IC50 (pM) Entry of NL4-3 | IC50 (pM) Replication of JRCSF |
|---|---|---|---|---|---|
| T-20 | YTSLIHSLIEESQNQQEKNEQELLELDKWASLWNWF | 36 | 24173 ± 2645 | 9413 ± 1187 | 5190 ± 306 |
| T20-TRM | YTSLIHSLIEESQNQQEKNEQELLELDK | 28 | >2000000 | >2000000 | >2000000 |
| LP-40 | YTSLIHSLIEESQNQQEKNEQELLELDK(C16) | 28 | 413 ± 95 | 439 ± 9 | 281 ± 40 |
| LP-41 | YTSLIHSLIEESQNQQEKNEQELLELD-AHK-K(C16) | 28 | 6603 ± 334 | 1572 ± 694 | 4892 ± 517 |
| LP-42 | YTSLIHSLIEESQNQQEKNEQELLELD-AEEA-K(C16) | 28 | 8716 ± 1101 | 2293 ± 914 | 6624 ± 326 |
| LP-43 | YTSLIHSLIEESQNQQEKNEQELLELD-PEG4-K(C16) | 28 | 11674 ± 2173 | 14140 ± 1044 | 5055 ± 807 |
| LP-44 | YTSLIHSLIEESQNQQEKNEQELLELD-PEG8-K(C16) | 28 | 15217 ± 730 | 95355 ± 31693 | 30173 ± 4257 |
| LP-45 | YTSLIHSLIEESQNQQEKNEQELLELD-PEG12-K(C16) | 28 | 35090 ± 3561 | 185256 ± 56783 | 45587 ± 8906 |
| LP-50 | YTSLIEELIKKSEEQQKKNEEELKKLEK(C16) | 28 | 21 ± 3 | 7 ± 1 | 23 ± 2 |
| LP-51 | LEANIEELIKKAEEQQKKNEEELKKLEK(C16) | 28 | 21 ± 10 | 6 ± 1 | 27 ± 5 |
| LP-52 | WEQKIEELLKKAEEQQKKNEEELKKLEK(C16) | 28 | 13 ± 1 | 4 ± 0 | 5 ± 1 |
| LP-53 | YTSLIHSLIEESQNQQEKNEQELLEK(C16) | 26 | 4722 ± 1706 | 8904 ± 1227 | 11151 ± 1937 |
| LP-54 | YTSLIEELIKKSEEQQKKNEEELK(C16) | 25 | 149 ± 48 | 301 ± 26 | 1796 ± 340 |
| LP-55 | WEQKIEELLKKAEEQQKKNEEELKK(C16) | 25 | 14 ± 2 | 8 ± 1 | 12 ± 1 |
| LP-56 | WEQKIEELLKKAEEQQKKNEEELKK-AEEA-K(C16) | 26 | 12 ± 2 | 9 ± 1 | 11 ± 2 |
| LP-57 | WEQKIEELLKKAEEQQKKNEEK(C16) | 23 | 213 ± 21 | 178 ± 38 | 1917 ± 440 |
| LP-58 | WEQKIEELLKKAEEQQKKNEK(C16) | 21 | 143000 ± 19911 | 110900 ± 3715 | 107033 ± 9473 |
| LP-59 | WEQKIEELLKKAEEQQKK(C16) | 18 | >900000 | 240800 ± 23649 | 210477 ± 25537 |
| LP-60 | SLIEELIKKSEEQQKKNEEELKKLEK(C16) | 26 | 55 ± 6 | 48 ± 6 | 62 ± 27 |
| LP-61 | IEELIKKSEEQQKKNEEELKKLEK(C16) | 24 | 85 ± 9 | 43 ± 9 | 126 ± 63 |
| LP-62 | EQKIEELLKKAEEQQKKNEEELKKLEK(C16) | 27 | 15 ± 1 | 5 ± 1 | 12 ± 1 |
| LP-63 | QKIEELLKKAEEQQKKNEEELKKLEK(C16) | 26 | 17 ± 5 | 6 ± 2 | 13 ± 2 |
| LP-64 | KIEELLKKAEEQQKKNEEELKKLEK(C16) | 25 | 128 ± 27 | 36 ± 1 | 25 ± 2 |
| LP-65 | IEELLKKAEEQQKKNEEELKKLEK(C16) | 24 | 14 ± 3 | 8 ± 3 | 7 ± 2 |
| LP-66 | EELLKKAEEQQKKNEEELKKLEK(C16) | 23 | 1008 ± 248 | 434 ± 71 | 1109 ± 193 |
| LP-67 | LLKAEEQQKKNEEELKKLEK(C16) | 21 | 3417 ± 419 | 627 ± 154 | 1527 ± 565 |
| LP-68 | AEEQQKKNEEELKKLEK(C16) | 17 | >250000 | >250000 | >250000 |
| LP-69 | IEELLKKAEEQQKKNEEELKK(C16) | 21 | 239 ± 16 | 125 ± 27 | 157 ± 29 |
| LP-70 | INNYTSLIEELIKKSEEQQKKNEEELKKLEK(C16) | 31 | 25 ± 3 | 21 ± 4 | 30 ± 10 |
| LP-71 | IEEYTKKIEELIKKSEEQQKKNEEELKKLEK(C16) | 31 | 27 ± 2 | 25 ± 3 | 55 ± 5 |
| LP-72 | VPYLEANIEELLKKAEEQQKKNEEELKKLEK(C16) | 31 | 23 ± 3 | 28 ± 1 | 24 ± 9 |
| LP-73 | VEELEKKIEELLKKAEEQQKKNEEELKKLEK(C16) | 31 | 33 ± 6 | 19 ± 3 | 42 ± 2 |
| LP-74 | WENEEKKIEEYTKKIEELLKKSEQKKEEELKKLEK(C16) | 38 | 110 ± 10 | 59 ± 11 | 59 ± 32 |
| LP-75 | EMTWEENEKKIEEYTKKIEELLKKSEQKKEEELKKLEK(C16) | 41 | 100 ± 22 | 65 ± 8 | 86 ± 26 |
| LP-80 | WEQKIEELLKKAEEQQKKNEEELKKLEK(C18) | 28 | 16 ± 2 | 2 ± 0 | 2 ± 0 |
| LP-81 | WEQKIEELLKKAEEQQKKNEEELKKLEK(C12) | 28 | 407 ± 57 | 160 ± 55 | 151 ± 31 |
| LP-82 | WEQKIEELLKKAEEQQKKNEEELKKLEK(C8) | 28 | 4216 ± 620 | 1255 ± 175 | 4478 ± 2055 |
| LP-83 | WEQKIEELLKKAEEQQKKNEEELKKLEKC(Chol) | 29 | 23 ± 2 | 2 ± 0 | 1 ± 0 |
| LP-84 | WEQKIEELLKKAEEQQKKNEEELKKLEK(DHS) | 28 | 13 ± 1 | 2 ± 1 | 3 ± 1 |
| LP-85 | WEQKIEELLKKAEEQQKKNEEELKKLEK(Toc) | 28 | 92 ± 7 | 4 ± 1 | 7 ± 1 |
| LP-86 | LEANIEELLKKAEEQQKKNEEELKKLEKC(Chol) | 29 | 29 ± 4 | 2 ± 0 | 1 ± 0 |
| LP-87 | LEANIEELLKKAEEQQKKNEEELKKLEK(DHS) | 28 | 19 ± 5 | 3 ± 1 | 2 ± 0 |
| LP-88 | EQKIEELLKKAEEQQKKNEEELKKLEK(C18) | 27 | 8 ± 2 | 4 ± 1 | 4 ± 1 |
| LP-89 | KIEELLKKAEEQQKKNEEELKKLEK(C18) | 25 | 59 ± 21 | 11 ± 3 | 12 ± 1 |
| LP-90 | IEELLKKAEEQQKKNEEELKKLEK(C18) | 24 | 6 ± 1 | 3 ± 1 | 2 ± 1 |
| LP-91 | WEQKIEELLKKAEEQQKKNEEELKK(C18) | 25 | 13 ± 1 | 7 ± 0 | 11 ± 2 |
| LP-92 | IEELLKKAEEQQKKNEEELKK(C18) | 21 | 189 ± 20 | 168 ± 21 | 229 ± 28 |
| LP-11 | EMTWEEWEKKIEEYTKKIEELLK-PEG8-K(C16) | 24 | 931 ± 68 | 201 ± 41 | 253 ± 40 |
| LP-19 | EMTWEEWEKKVEELEKKIEELLK-PEG8-K(C16) | 24 | 296 ± 45 | 95 ± 18 | 92 ± 11 |
| C34-Chol | WMEWDREINNYTSLIHSLIEESQNQQEKNEQELL-GSG-C(Chol) | 38 | 316 ± 62 | 24 ± 2 | 37 ± 5 |
| C34-C16 | WMEWDREINNYTSLIHSLIEESQNQQEKNEQELLK(C16) | 35 | 247 ± 28 | 65 ± 25 | 109 ± 13 |

Figure 2

| HIV-1 strain | Subtype | IC$_{50}$ (pM) | | | | | | | | | | | |
|---|---|---|---|---|---|---|---|---|---|---|---|---|---|
| | | T-20 | LP-40 | LP-50 | LP-51 | LP-52 | LP-55 | LP-65 | LP-80 | LP-85 | LP-90 | LP-19 | C34-Chol |
| 92RW020 | A | 101337 | 16617 | 596 | 273 | 29 | 41 | 503 | 10 | 92 | 15 | 283 | 90 |
| 92UG037.8 | A | 5361 | 2466 | 19 | 17 | 18 | 20 | 20 | 4 | 34 | 8 | 345 | 116 |
| 398-F1_F6_20 | A | 12690 | 3584 | 12 | 15 | 7 | 11 | 6 | 1 | 11 | 6 | 113 | 15 |
| PVO | B | 71948 | 2832 | 24 | 33 | 31 | 122 | 25 | 13 | 67 | 23 | 1380 | 106 |
| REJO4541 | B | 57733 | 10129 | 9 | 8 | 6 | 36 | 18 | 1 | 18 | 16 | 135 | 67 |
| SF162 | B | 26503 | 5138 | 27 | 26 | 16 | 25 | 30 | 3 | 18 | 5 | 405 | 32 |
| JRFL | B | 8998 | 1756 | 39 | 74 | 57 | 45 | 43 | 10 | 84 | 12 | 2160 | 115 |
| SC422661.8 | B | 20649 | 18684 | 29 | 7 | 8 | 51 | 52 | 3 | 19 | 39 | 133 | 73 |
| AC10.0.29 | B | 13597 | 1092 | 6 | 9 | 10 | 8 | 7 | 6 | 19 | 3 | 105 | 35 |
| TRO.11 | B | 6175 | 3095 | 26 | 27 | 18 | 20 | 31 | 4 | 15 | 9 | 323 | 29 |
| X2278_C2_B6 | B | 6423 | 1824 | 13 | 11 | 6 | 1 | 12 | <1 | 4 | 2 | 70 | 9 |
| B01 | B' | 89185 | 8630 | 188 | 145 | 12 | 19 | 192 | 3 | 25 | 18 | 350 | 46 |
| B02 | B' | 7695 | 906 | 23 | 29 | 16 | 35 | 24 | 9 | 53 | 16 | 690 | 61 |
| B04 | B' | 5008 | 1137 | 23 | 44 | 8 | 28 | 25 | 4 | 23 | 17 | 480 | 78 |
| 43-22 | B' | 30648 | 1354 | 5 | 8 | 6 | 2 | 14 | 3 | 6 | 4 | 100 | 26 |
| Du156 | C | 14433 | 10538 | 6 | 8 | 5 | 15 | 5 | 1 | 14 | 4 | 150 | 27 |
| ZM53M.PB12 | C | 34000 | 4634 | 21 | 19 | 15 | 21 | 27 | 8 | 47 | 7 | 295 | 83 |
| CAP210.2.00.E8 | C | 140667 | 29190 | 35 | 62 | 23 | 223 | 100 | 11 | 76 | 29 | 465 | 78 |
| CAP45.2.00.G3 | C | 170900 | 21740 | 9 | 12 | 9 | 6 | 6 | 3 | 16 | 2 | 245 | 11 |
| CE703010217_B6 | C | 43107 | 3523 | 27 | 20 | 9 | 27 | 18 | 6 | 50 | 11 | 475 | 83 |
| HIV_25710-2.43 | C | 14730 | 4349 | 26 | 27 | 17 | 46 | 40 | 3 | 44 | 16 | 200 | 47 |
| CE1176_A3 | C | 4656 | 1581 | 10 | 15 | 13 | 12 | 11 | 3 | 41 | 9 | 385 | 83 |
| X1632-S2-B10 | G | 15487 | 2267 | 19 | 32 | 27 | 5 | 34 | 6 | 48 | 28 | 277 | 92 |
| 246_F3_C10_2 | A/C | 41237 | 3888 | 20 | 26 | 11 | 11 | 16 | 4 | 40 | 7 | 530 | 40 |
| AE03 | A/E | 8657 | 3615 | 16 | 17 | 9 | 6 | 41 | 3 | 11 | 14 | 128 | 16 |
| GX11.13 | A/E | 11720 | 815 | 10 | 14 | 16 | 14 | 13 | 5 | 41 | 25 | 597 | 142 |
| SHX335.24 | A/E | 48420 | 25968 | 11 | 16 | 7 | 19 | 12 | 3 | 30 | 3 | 130 | 47 |
| CNE8 | A/E | 35240 | 3459 | 40 | 31 | 12 | 13 | 316 | 4 | 58 | 23 | 410 | 114 |
| CNE55 | A/E | 23047 | 2684 | 14 | 8 | 12 | 2 | 11 | 1 | 19 | 3 | 190 | 39 |
| CH64.20 | B/C | 50693 | 4962 | 27 | 29 | 27 | 28 | 33 | 12 | 51 | 10 | 143 | 43 |
| CH070.1 | B/C | 163316 | 6269 | 37 | 38 | 35 | 114 | 42 | 29 | 185 | 32 | 1395 | 213 |
| CH110 | B/C | 33790 | 3631 | 6 | 8 | 13 | 16 | 8 | 3 | 35 | 8 | 147 | 41 |
| CH120.6 | B/C | 74063 | 4954 | 18 | 19 | 18 | 98 | 23 | 11 | 130 | 25 | 1525 | 101 |
| CH119.10 | B/C | 22843 | 2222 | 19 | 11 | 11 | 10 | 25 | 5 | 29 | 11 | 120 | 41 |
| BJOX002000.03.2 | B/C | 34383 | 3349 | 36 | 31 | 35 | 42 | 36 | 8 | 74 | 14 | 225 | 68 |
| Average IC$_{50}$ (pM) | | 41410 | 6369 | 41 | 33 | 16 | 34 | 52 | 6 | 44 | 14 | 439 | 66 |

Figure 3

| Virus | IC$_{50}$ (nM) | | | | | | | | | |
|---|---|---|---|---|---|---|---|---|---|---|
| | T-20 | LP-40 | LP-50 | LP-51 | LP-52 | LP-55 | LP-65 | LP-80 | LP-85 | LP-90 |
| NL4-3$_{WT}$ | 152.23 | 36 | 0.08 | 0.03 | 0.01 | 0.11 | 0.15 | <0.01 | 0.02 | 0.05 |
| NL4-3$_{D36G}$ | 13.65 | 0.5 | 0.01 | 0.01 | 0.01 | 0.01 | 0.01 | <0.01 | 0.02 | <0.01 |
| NL4-3$_{I37T}$ | 1001.19 | 415.27 | 1.07 | 0.59 | 0.16 | 1.65 | 1.04 | 0.12 | 0.03 | 0.58 |
| NL4-3$_{V38A}$ | 2780 | 1548 | 6.53 | 1.77 | 0.37 | 4.77 | 6.62 | 0.55 | 0.61 | 6.41 |
| NL4-3$_{V38M}$ | 1319.73 | 1368 | 1.45 | 0.4 | 0.2 | 3.05 | 6.96 | 0.26 | 0.28 | 5.33 |
| NL4-3$_{Q40H}$ | 2147.37 | 1814 | 3.76 | 0.58 | 0.1 | 8.2 | 5.59 | 0.33 | 0.32 | 3.59 |
| NL4-3$_{N43K}$ | 729.12 | 517.43 | 5.87 | 0.99 | 0.31 | 23.44 | 5.51 | 0.53 | 1.12 | 5.35 |
| NL4-3$_{D36S/V38M}$ | 565.17 | 1134.33 | 1.76 | 0.38 | 0.13 | 1.18 | 3.57 | 0.21 | 0.22 | 2.88 |
| NL4-3$_{I37T/N43K}$ | >4000 | 3296 | 142.03 | 13.11 | 1.86 | >50 | 86.63 | 9.91 | 13.98 | 46.33 |
| NL4-3$_{V38A/N42T}$ | 2756 | 1745.13 | 60.32 | 8.3 | 1.22 | 44.81 | 69.93 | 3.52 | 4.6 | 49.66 |
| HIV-2$_{ROD}$ | 263.68 | 636.43 | 0.09 | 0.08 | 0.06 | >20 | 0.11 | 0.03 | 0.47 | 0.22 |
| SIV$_{239}$ | 533.85 | >750 | 0.05 | 0.04 | 0.02 | 0.9 | 0.07 | 0.02 | 0.04 | 0.03 |
| SIV$_{PBJ}$ | 357.07 | >750 | 0.06 | 0.07 | 0.02 | 4.31 | 0.04 | 0.02 | 0.51 | 0.12 |

| Inhibitor | Sequence structure | Number of amino acids | Helical content (%) | Tmvalue(℃) |
|---|---|---|---|---|
| T-20 | YTSLIHSLIEESQNQQEKNEQELLELDKWASLWNWF | 36 | 48.6 | 43.9 |
| T20-TRM | YTSLIHSLIEESQNQQEKNEQELLELDK | 28 | 18.8 | NA |
| LP-40 | YTSLIHSLIEESQNQQEKNEQELLELDK(C16) | 28 | 57.7 | 51.3 |
| LP-41 | YTSLIHSLIEESQNQQEKNEQELLELD-AHX-K(C16) | 28 | 49.0 | 50.5 |
| LP-42 | YTSLIHSLIEESQNQQEKNEQELLELD-AEEA-K(C16) | 28 | 51.6 | 51.1 |
| LP-43 | YTSLIHSLIEESQNQQEKNEQELLELD-PEG4-K(C16) | 28 | 52.3 | 51.2 |
| LP-44 | YTSLIHSLIEESQNQQEKNEQELLELD-PEG8-K(C16) | 28 | 51.2 | 49.4 |
| LP-45 | YTSLIHSLIEESQNQQEKNEQELLELD-PEG12-K(C16) | 28 | 50.6 | 46.6 |
| LP-50 | YTSLIEELIKKSEEQQKKNEEELKKLEK(C16) | 28 | 55.6 | 63.3 |
| LP-51 | LEANIEELLKKAEEQQKKNEEELKKLEK(C16) | 28 | 54.1 | 72.0 |
| LP-52 | WEQKIEELLKKAEEQQKKNEEELKKLEK(C16) | 28 | 63.8 | 79.1 |
| LP-53 | YTSLIHSLIEESQNQQEKNEQELLEK(C16) | 26 | 53.9 | 43.0 |
| LP-54 | YTSLIEELIKKSEEQQKKNEEELKK(C16) | 25 | 49.6 | 47.1 |
| LP-55 | WEQKIEELLKKAEEQQKKNEEELKK(C16) | 25 | 50.6 | 63.1 |
| LP-56 | WEQKIEELLKKAEEQQKKNEEELKK-AEEA-K(C16) | 26 | 43.3 | 63.1 |
| LP-57 | WEQKIEELLKKAEEQQKKNEEEK(C16) | 23 | 59.2 | 43.0 |
| LP-58 | WEQKIEELLKKAEEQQKKNEK(C16) | 21 | 38.2 | NA |
| LP-59 | WEQKIEELLKKAEEQQKK(C16) | 18 | 27.1 | NA |
| LP-60 | SLIEELIKKSEEQQKKNEEELKKLEK(C16) | 26 | 38.9 | 58.1 |
| LP-61 | IEELIKKSEEQQKKNEEELKKLEK(C16) | 24 | 54.4 | 59.1 |
| LP-62 | EQKIEELLKKAEEQQKKNEEELKKLEK(C16) | 27 | 57.0 | 73.1 |
| LP-63 | QKIEELLKKAEEQQKKNEEELKKLEK(C16) | 26 | 48.1 | 70.1 |
| LP-64 | KIEELLKKAEEQQKKNEEELKKLEK(C16) | 26 | 40.1 | 72.0 |
| LP-65 | IEELLKKAEEQQKKNEEELKKLEK(C16) | 24 | 63.0 | 72.1 |
| LP-66 | EELLKKAEEQQKKNEEELKKLEK(C16) | 23 | 64.0 | 60.1 |
| LP-67 | LLEQAEEQQKKNEEELKKLEK(C16) | 21 | 50.1 | 48.1 |
| LP-68 | AEEQKKKNEEELKKLEK(C16) | 17 | 53.3 | 60.1 |
| LP-69 | IEELLKKAEEQQKKNEEELKK(C16) | 21 | 44.9 | 51.0 |
| LP-70 | INNYTSLIEELIKKSEEQQKKNEEELKKLEK(C16) | 31 | 44.8 | 69.1 |
| LP-71 | IEEYTKKIEEILKKSEEQQKKNEEELKKLEK(C16) | 31 | 57.2 | 69.1 |
| LP-72 | VPYLEANIEELLKKAEEQQKKNEEELKKLEK(C16) | 31 | 43.5 | 74.1 |
| LP-73 | VEELEKKIEELLKKAEEQQKKNEEELKKLEK(C16) | 31 | 86.6 | 80.1 |
| LP-74 | WEEWEKKIEEYTKKIEEILKKSEEQQKKNEEELKKLEK(C16) | 38 | 58.3 | 67.1 |
| LP-75 | EMTWEEWEKKIEEYTKKIEEILKKSEEQQKKNEEELKKLEK(C16) | 41 | 60.5 | 67.1 |
| LP-80 | WEQKIEELLKKAEEQQKKNEEELKKLEK(C18) | 28 | 57.4 | 79.0 |
| LP-81 | WEQKIEELLKKAEEQQKKNEEELKKLEK(C12) | 28 | 49.0 | 74.1 |
| LP-82 | WEQKIEELLKKAEEQQKKNEEELKKLEK(C8) | 28 | 39.1 | 65.1 |
| LP-83 | WEQKIEELLKKAEEQQKKNEEELKKLEKC(Chol) | 29 | 49.4 | 78.1 |
| LP-84 | WEQKIEELLKKAEEQQKKNEEELKKLEK(DHS) | 28 | 62.9 | 80.1 |
| LP-85 | WEQKIEELLKKAEEQQKKNEEELKKLEK(Toc) | 28 | 44.7 | 76.1 |
| LP-86 | LEANIEELLKKAEEQQKKNEEELKKLEKC(Chol) | 29 | 47.7 | 76.1 |
| LP-87 | LEANIEELLKKAEEQQKKNEEELKKLEK(DHS) | 28 | 42.7 | 71.1 |
| LP-88 | EQKIEELLKKAEEQQKKNEEELKKLEK(C18) | 27 | 51.7 | 76.5 |
| LP-89 | KIEELLKKAEEQQKKNEEELKKLEK(C18) | 25 | 50.9 | 70.0 |
| LP-90 | IEELLKKAEEQQKKNEEELKKLEK(C18) | 24 | 41.3 | 71.1 |
| LP-91 | WEQKIEELLKKAEEQQKKNEEELKK(C18) | 25 | 55.0 | 61.0 |
| LP-92 | IEELLKKAEEQQKKNEEELKK(C18) | 21 | 37.8 | 55.1 |

Figure 6

SEQUENCE LISTING

<160> NUMBER OF SEQ ID NOS: 12

<210> SEQ ID NO 1
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 1

Trp Glu Gln Lys Ile Glu Glu Leu Leu Lys Lys Ala Glu Glu Gln Gln
1               5                   10                  15

Lys Lys Asn Glu Glu Glu Leu Lys Lys Leu Glu Lys
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 2

Leu Glu Ala Asn Ile Glu Glu Leu Leu Lys Lys Ala Glu Glu Gln Gln
1               5                   10                  15

Lys Lys Asn Glu Glu Glu Leu Lys Lys Leu Glu Lys
            20                  25

<210> SEQ ID NO 3
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 3

Tyr Thr Ser Leu Ile Glu Glu Leu Ile Lys Lys Ser Glu Glu Gln Gln
1               5                   10                  15

Lys Lys Asn Glu Glu Glu Leu Lys Lys Leu Glu Lys
            20                  25

<210> SEQ ID NO 4
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 4

Glu Gln Lys Ile Glu Glu Leu Leu Lys Lys Ala Glu Glu Gln Gln Lys
1               5                   10                  15

Lys Asn Glu Glu Glu Leu Lys Lys Leu Glu Lys
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 5

Gln Lys Ile Glu Glu Leu Leu Lys Lys Ala Glu Glu Gln Gln Lys Lys
1               5                   10                  15

Asn Glu Glu Glu Leu Lys Lys Leu Glu Lys
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 6

Ser Leu Ile Glu Glu Leu Ile Lys Lys Ser Glu Glu Gln Gln Lys Lys
1               5                   10                  15

Asn Glu Glu Glu Leu Lys Lys Leu Glu Lys
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 7

Lys Ile Glu Glu Leu Leu Lys Lys Ala Glu Glu Gln Gln Lys Lys Asn
1               5                   10                  15

Glu Glu Glu Leu Lys Lys Leu Glu Lys
            20                  25

<210> SEQ ID NO 8
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 8

Ile Glu Glu Leu Leu Lys Lys Ala Glu Glu Gln Gln Lys Lys Asn Glu
1               5                   10                  15

Glu Glu Leu Lys Lys Leu Glu Lys
            20

<210> SEQ ID NO 9
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 9

Ile Glu Glu Leu Ile Lys Lys Ser Glu Glu Gln Gln Lys Lys Asn Glu
1               5                   10                  15

Glu Glu Leu Lys Lys Leu Glu Lys
            20

<210> SEQ ID NO 10
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 10

Trp Glu Gln Lys Ile Glu Glu Leu Leu Lys Lys Ala Glu Glu Gln Gln
1               5                   10                  15

```
Lys Lys Asn Glu Glu Glu Leu Lys Lys
            20                  25

<210> SEQ ID NO 11
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 11

Trp Glu Gln Lys Ile Glu Glu Leu Leu Lys Lys Ala Glu Glu Gln Gln
1               5                   10                  15

Lys Lys Asn Glu Glu Glu Leu Lys Lys Leu Glu Lys Cys
            20                  25

<210> SEQ ID NO 12
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 12

Leu Glu Ala Asn Ile Glu Glu Leu Leu Lys Lys Ala Glu Glu Gln Gln
1               5                   10                  15

Lys Lys Asn Glu Glu Glu Leu Lys Lys Leu Glu Lys Cys
            20                  25
```

LIPOPEPTIDE FOR POTENTLY INHIBITING HIV, DERIVATIVE THEREOF, PHARMACEUTICAL COMPOSITION THEREOF AND USE THEREOF

RELATED APPLICATIONS

This application is a national stage filing under 35 U.S.C. § 371 of International Patent Application Serial No. PCT/CN2017/080860, filed Apr. 18, 2017, the entire contents of which is incorporated herein by reference.

TECHNICAL FIELD

The present invention relates to a lipopeptide for potently inhibiting HIV, derivative thereof, or pharmaceutical composition thereof, to and use thereof in the biomedicine field.

BACKGROUND ART

Acquired immune deficiency syndrome (AIDS) is an infectious disease that seriously harms human health and social development at present. Human immunodeficiency virus that causes AIDS is divided into two types, i.e., HIV-1 and HIV-2. There are about 36 millions of people who are infected with HIV in the world, and HIV-1 is the main pathogen (www.unaids.org). At present, there is no effective AIDS vaccine available, and drugs that block the replication of the virus at different stages play a major role in the treatment and prevention of HIV infection. Currently, drugs used in clinical treatment mainly include nucleoside reverse transcriptase inhibitors, non-nucleoside reverse transcriptase inhibitors, protease inhibitors, viral entry inhibitors, and integrase inhibitors (www.fda.gov). A highly effective antiviral treatment regimen that has been widely used clinically, i.e., so-called "cocktail" therapy, consists mainly of 3-4 reverse transcriptase inhibitors and protease inhibitors. Due to the persistence of HIV infection, it is required to administer drugs to patients for a long period of time, easily leading to drug resistance, which seriously affects the clinical treatment effect [1]. Accordingly, the development of new anti-HIV drugs has always been an important strategy to prevent and control AIDS.

Unlike other types of drugs, HIV entry inhibitors function at the early stages of virus replication, and act by blocking the virus from entering the target cells, as if "the enemy is rejected outside the country", thus the HIV entry inhibitors have obvious advantages in both treatment and prevention. However, only two HIV entry inhibitors are currently approved for clinical application: the first one is the HIV membrane fusion inhibitor enfuvirtide (also known as T-20), which is a polypeptide drug having 36 amino acids derived from the HIV fusion protein gp41, and the second one is a coreceptor CCR5 antagonist Maraviroc. Due to the successful development of the two HIV entry inhibitors, new means for the clinical treatment of AIDS are added. Unfortunately, it is required to administer T-20 at a large dose every day (90 mg subcutaneous injection twice daily) due to its relatively low activity, and T-20 easily leads to drug resistance, and Maraviroc is selectively against CCR5-tropic virus and is ineffective against CRCR4-tropic virus [2].

Entry of HIV into target cells is mediated by its surface envelope glycoprotein (Env) which is formed by binding a surface subunit gp120 to a transmembrane subunit gp41 via a non-covalent bond and is a trimeric structure in natural state [3]. First of all, the sequential binding of gp120 to the cellular receptor CD4 receptor and coreceptor (such as CCR5 or CXCR4) triggers a cascade of conformational change in gp120, further exposes the gp41 and activates the membrane fusion function of the gp41. Gp41 is structurally divided into three parts: an extramembrane region, a transmembrane region (TM) and an intramembrane region, wherein extramembrane region further includes several important functional regions, such as N-terminal hydrophobic fusion peptide (FP) region, N-terminal heptad repeat region (NHR), C-terminal heptad repeat region (CHR), and membrane proximal external region (MPER) (FIG. 1). As early as 1997, by analyzing the crystal structure of a complex of NHR-derived polypeptide N36 and CHR-derived polypeptide C34, a typical six-stranded α-helical bundle structure (6-HB) is found, in which three NHRs form a centrally located helical trimer by interaction of amino acids at the a and d positions, and the amino acids at the e and g positions are exposed to around the outside of the central trimer and interact with the three CHR helices at the a and d position [4]. The three CHR helices are respectively combined in a groove formed by three NHR helices in an antiparallel orientation, similar to a three stacked hairpin structure. Based on the 6-HB structure, the mechanism of HIV membrane fusion is deeply understood, the exposed gp41 fusion peptide is firstly inserted into the membrane of a target cell, then the CHR is reversely bound to the NHR, the viral membrane is brought close to the membrane of the target cell to result in the fusion by formation of stable 6-HB, whereby the HIV genetic material enters into the target cell eventually. The 6-HB structure also reveals that there is a distinct hydrophobic deep pocket formed at C-terminus of the NHR helices, while the three amino acids at the N-terminus of the CHR, i.e., the so-called pocket-binding domain (PBD), are inserted into the NHR hydrophobic pocket, wherein the interaction between them plays an important role in stabilizing the 6-HB structure and is therefore necessary for HIV infection. For a long period of time, the NHR hydrophobic pocket has been recognized as an important target for anti-HIV drugs, and the PBD motif of CHR is the key to design anti-HIV peptide inhibitors [5,6].

Previous studies have shown that polypeptides derived from the gp41 CHR or NHR have significant anti-HIV activity, mainly competitively binds to corresponding NHR or CHR to prevent the formation of viral itself 6-HB structure, thereby blocks the fusion of the virus and cell membrane [6]. Typically, the antiviral activity of a prototype CHR polypeptide is significantly higher than a prototype NHR polypeptide. The drug T-20 belongs to one of CHR polypeptides, and its sequence is shown in FIG. 1, which corresponds to the amino acid sequence at the positions 127 to 162 of gp41 from HIV-1 strain HXB2. One of the structural features of the sequence of T-20 is that it has a hydrophobic tryptophan-rich motif (TRM: WASLWNWF) at its C-terminus, but it lacks a PBD sequence (WMEW-DREI) at its N-terminus. It has been found by studies that TRM of T-20 mediates the binding of the polypeptide to the cell membrane lipid and it is therefore considered to be a lipid-binding domain (LBD), and this property is important for the antiviral activity of T-20. Due to obvious defects of T-20 in clinical application, research and development of a new generation of HIV membrane fusion inhibitors has always been an international hot topic, but most of studies are based on the CHR polypeptide C34 containing 34 amino acids as a template, and use of T-20 as a template is rarely reported. This may be because: 1) C34 is used for the analysis of the structure of the 6-HB at first, and corresponds to the amino acid sequence at positions 117-150 of the gp41 which is considered to be the core CHR sequence; 2) C34 contains an important PBD sequence at N-terminus, and C34 has a NHR binding activity and antiviral activity higher than T-20; and 3) C34 has significantly enhanced inhibitory activity against T-20 resistant virus strains. Newly developed HIV membrane fusion inhibitors such as T2635, SC35EK, SC29EK, Sifuvirtide (SFT), Albuvirtide (ABT), C34-Chol, and the like, are all obtained by optimization and/or modification of the sequence of C34 [6,7], and they do also have better inhibitory activity and stability than T-20.

Recently, the discovery of the "M-T hook" structure of CHR polypeptides has provided a new approach to design highly active HIV membrane fusion inhibitors [8-10]. It has been shown by studies that the addition of two amino acid residues (i.e., Met115 and Thr116) that can form an M-T hook structure at the front of PBD of CHR polypeptide can significantly increase the binding activity to a target sequence and antiviral activity of inhibitors, especially enhance the activity of inhibitors against T-20 resistant strains, and significantly enhance genetic barrier for drug resistance of the inhibitors [11, 12]. The M-T hook structure also makes it possible to design short peptides targeting NHR hydrophobic pocket, such as MT-SC22EK with a length of 24 amino acids and HP23 and 2P23 with a length of 23 amino acids [13-15]. These short peptides display higher antiviral activity and binding activity to target sequence than other long sequence polypeptides. 2P23 is not only effective against HIV-1 and T-20-resistant strains thereof, but also very effective against HIV-2 and simian immunodeficiency virus (SIV), and thus 2P23 is a broad-spectrum viral membrane fusion inhibitor [13].

The lipid raft of cell membrane is rich in cholesterol and sphingomyelin as well as many transmembrane proteins and receptors (e.g., HIV receptor CD4), and plays an important role in virus entry and infection. On the other hand, an enveloped viral lipid bilayer membrane structure derived from cell membrane is also rich in cholesterol and sphingomyelin, and is involved in maintaining the normal structure and function of viral envelope proteins [16,17]. During HIV entry into a target cell, the lipid raft and the lipids (e.g., cholesterol and sphingomyelin) contained therein provide a suitable platform for the interaction between the gp120 of virus and cellular receptor CD4 or coreceptor. Studies show that by anchoring an viral membrane fusion inhibitor (for example, peptides, proteins, antibodies, and so on) to the surface of cell membrane, local concentration of the inhibitor at the cell membrane can be increased, thereby significantly increasing its antiviral activity [18-20]. In fact, HIV membrane fusion inhibitors based on CHR polypeptide, such as T-20, T-1249 and Sifuvirtide, these polypeptides themselves have the ability to interact with cell membrane [21-23]. Peisajovich et al. revealed the important role of TRM in the interaction between TRM of T-20 and cell membrane to exhibit antiviral function by mutational analysis of amino acid residues of TRM of T-20 and modification of lipophilic functional group at the C-terminus thereof [24]. Expression of T-20 on the surface of cell membrane by a recombinant construction technique can also significantly increase its inhibitory activity against the virus [25, 26]. Recent studies have also shown that the chemical modification of the polypeptide by use of lipids, the so-called "lipopeptides", can increase the ability to target cell membrane and antiviral activity of the polypeptide, and significantly improve the stability and biological half-life of the polypeptide [18-20, 27]. Studies on HIV membrane fusion inhibitors have shown that increase in the activity of CHR polypeptides is dependent on the C-terminal modification, while N-terminal modification is suitable for NHR polypeptides, which is consistent with the structure of 6-HB and the mechanism of viral membrane fusion. That is to say, C-terminal anchoring is beneficial to a CHR polypeptide for binding the NHR of virus. In contrast, to a NHR polypeptide, the N-terminal cell membrane anchoring is more beneficial for binding the CHR of virus [19, 28, 29]. Just like to the design of non-modified CHR polypeptides, the design of lipopeptides as HIV membrane fusion inhibitors has focused on use of the C34 containing PBD as a template. A representative example is the lipopeptide C34-Chol (see FIG. 1) designed by Ingallinella et al. in 2009, it is obtained by linking cholesterol to the C-terminus of C34 via a flexible linker and cysteine, and based on the antiviral results, it is considered to be an HIV membrane fusion inhibitor having the highest activity and its metabolic half-life in animals is also significantly prolonged [20]. In the inventors' laboratory three lipid compounds, palmitic acid (C16), cholesterol and dihydrosphingosine, are used to modify the short peptides HP23 and HP23L targeting NHR pockets, respectively, to prepare a group of lipopeptides having high activity, wherein the in vivo stability of the LP-11 is also greatly improved [18]. Recently, in the inventors' laboratory, the palmitic acid-modified lipopeptide LP-19 is obtained on the basis of a broad-spectrum anti-HIV short peptide 2P23, which has higher antiviral activity and druggability [30]. These advances on studies have laid a solid theoretical foundation and technical routes for the design of new HIV membrane fusion inhibitors.

THE REFERENCES

1. Flexner C. HIV drug development: the next 25 years. Nat Rev Drug Discov 2007, 6:959-966.
2. Este J A, Telenti A. HIV entry inhibitors. Lancet 2007, 370:81-88.
3. Eckert D M, Kim P S. Mechanisms of viral membrane fusion and its inhibition. Annu Rev Biochem 2001, 70:777-810.
4. Chan D C, Fass D, Berger J M, Kim P S. Core structure of gp41 from the HIV envelope glycoprotein. Cell 1997, 89:263-273.
5. Chan D C, Chutkowski C T, Kim P S. Evidence that a prominent cavity in the coiled coil of HIV type 1 gp41 is an attractive drug target. Proc Natl Acad Sci USA 1998, 95:15613-15617.
6. He Y. Synthesized peptide inhibitors of HIV-1 gp41-dependent membrane fusion. Curr Pharm Des 2013, 19:1800-1809.
7. Eggink D, Berkhout B, Sanders R W. Inhibition of HIV-1 by fusion inhibitors. Curr Pharm Des 2010, 16:3716-3728.
8. Chong H, Yao X, Sun J, Qiu Z, Zhang M, Waltersperger S, et al. The M-T hook structure is critical for design of HIV-1 fusion inhibitors. J Biol Chem 2012, 287:34558-34568.
9. Chong H, Qiu Z, Su Y, He Y. The N-Terminal T-T Motif of a Third-Generation HIV-1 Fusion Inhibitor Is Not Required for Binding Affinity and Antiviral Activity. J Med Chem 2015, 58:6378-6388.
10. Chong H, Yao X, Qiu Z, Qin B, Han R, Waltersperger S, et al. Discovery of critical residues for viral entry and inhibition through structural Insight of HIV-1 fusion inhibitor CP621-652. J Biol Chem 2012, 287:20281-20289.
11. Chong H, Yao X, Qiu Z, Sun J, Qiao Y, Zhang M, et al. The M-T hook structure increases the potency of HIV-1 fusion inhibitor sifuvirtide and overcomes drug resistance. J Antimicrob Chemother 2014, 69:6759.
12. Chong H, Qiu Z, Sun J, Qiao Y, Li X, He Y. Two M-T hook residues greatly improve the antiviral activity and resistance profile of the HIV-1 fusion inhibitor SC29EK. Retrovirology 2014, 11:40.
13. Xiong S, Borrego P, Ding X, Zhu Y, Martins A, Chong H, et al. A helical short-peptide fusion inhibitor with highly potent activity against human immunodeficiency virus type 1 (HIV-1), HIV-2, and simian immunodeficiency virus. J Virol 2017, 91:e01839-16.
14. Chong H, Qiu Z, Su Y, Yang L, He Y. Design of a highly potent HIV-1 fusion inhibitor targeting the gp41 pocket. AIDS 2015, 29:13-21.
15. Chong H, Yao X, Qiu Z, Sun J, Zhang M, Waltersperger S, et al. Short-peptide fusion inhibitors with high potency against wild-type and enfuvirtide-resistant HIV-1. FASEB J 2013, 27:1203-1213.
16. Brugger B, Glass B, Haberkant P, Leibrecht I, Wieland F T, Krausslich H G. The HIV lipidome: a raft with an unusual composition. Proc Natl Acad Sci USA 2006, 103:2641-2646.
17. Ono A, Freed E O. Plasma membrane rafts play a critical role in HIV-1 assembly and release. Proc Natl Acad Sci USA 2001, 98:13925-13930.
18. Chong H, Wu X, Su Y, He Y. Development of potent and long-acting HIV-1 fusion inhibitors. AIDS 2016, 30:1187-1196.
19. Wexler-Cohen Y, Shai Y. Membrane-anchored HIV-1 N-heptad repeat peptides are highly potent cell fusion inhibitors via an altered mode of action. PLoS Pathog 2009, 5:e1000509.
20. Ingallinella P, Bianchi E, Ladwa N A, Wang Y J, Hrin R, Veneziano M, et al. Addition of a cholesterol group to an HIV-1 peptide fusion inhibitor dramatically increases its antiviral potency. Proc Natl Acad Sci USA 2009, 106: 5801-5806.
21. Matos P M, Castanho M A, Santos N C. HIV-1 fusion inhibitor peptides enfuvirtide and T-1249 interact with erythrocyte and lymphocyte membranes. PLoS One 2010, 5:e9830.
22. Franquelim H G, Loura L M, Santos N C, Castanho M A. Sifuvirtide screens rigid membrane surfaces. establishment of a correlation between efficacy and membrane domain selectivity among HIV fusion inhibitor peptides. J Am Chem Soc 2008, 130:6215-6223.
23. Veiga A S, Santos N C, Loura L M, Fedorov A, Castanho M A. HIV fusion inhibitor peptide T-1249 is able to insert or adsorb to lipidic bilayers. Putative correlation with improved efficiency. J Am Chem Soc 2004, 126:14758-14763.
24. Peisajovich S G, Gallo S A, Blumenthal R, Shai Y. C-terminal octylation rescues an inactive T20 mutant: implications for the mechanism of HIV/SIMIAN immunodeficiency virus-induced membrane fusion. J Biol Chem 2003, 278:21012-21017.
25. Hildinger M, Dittmar M T, Schult-Dietrich P, Fehse B, Schnierle B S, Thaler S, et al. Membrane-anchored peptide inhibits human immunodeficiency virus entry. J Virol 2001, 75:3038-3042.
26. Egelhofer M, Brandenburg G, Martinius H, Schult-Dietrich P, Melikyan G, Kunert R, et al. Inhibition of human immunodeficiency virus type 1 entry in cells expressing gp41-derived peptides. J Virol 2004, 78:568-575.
27. Ashkenazi A, Viard M, Unger L, Blumenthal R, Shai Y. Sphingopeptides: dihydrosphingosine-based fusion inhibitors against wild-type and enfuvirtide-resistant HIV-1. FASEB J 2012, 26:4628-4636.
28. Wexler-Cohen Y, Shai Y. Demonstrating the C-terminal boundary of the HIV 1 fusion conformation in a dynamic ongoing fusion process and implication for fusion inhibition. FASEB J 2007, 21:3677-3684.
29. Wexler-Cohen Y, Ashkenazi A, Viard M, Blumenthal R, Shai Y. Virus-cell and cell-cell fusion mediated by the HIV-1 envelope glycoprotein is inhibited by short gp41 N-terminal membrane-anchored peptides lacking the critical pocket domain. FASEB J 2010, 24:4196-4202.
30. Chong H, Xue J, Xiong S, Cong Z, Ding X, Zhu Y, Liu Z, Chen T, Feng Y, He L, Guo Y, Wei Q, Zhou Y, Qin C, He Y. A lipopeptide HIV-1/2fusion inhibitor with highly potent in vitro, ex vivo and in vivo antiviral activity. J Virol 2017, 91: e00288-17.

DISCLOSURES OF THE PRESENT INVENTION

The technical problem to be solved by the present invention is how to potently inhibit HIV.

In order to solve the above technical problem, the present invention provides a potent HIV membrane fusion inhibitor. The potent HIV membrane fusion inhibitor provided by the present invention is a lipopeptide having a potent inhibitory activity against HIV, a pharmaceutically acceptable salt thereof, or a derivative thereof, wherein the lipopeptide is the following a) or b):

a) a lipopeptide formed by linking a polypeptide having an antiviral activity to a lipophilic compound linked to the carboxyl-terminus of the polypeptide;

b) a lipopeptide formed by linking a polypeptide having an antiviral activity to a terminal protecting group and a lipophilic compound linked to the carboxyl-terminus of the polypeptide, wherein the terminal protecting group is an amino terminal protecting group and/or a carboxyl terminal protecting group;

in the a) and b), the polypeptide is any one of P1 to P5;

the P1 has a sequence as shown in the following Formula I, $$X_1X_2X_3X_4X_5X_6X_7X_8X_9X_{10}X_{11}X_{12}X_{13}$$
$$X_{14}X_{15}X_{16}X_{17}X_{18}X_{19}X_{20}X_{21}X_{22}X_{23}$$
$$X_{24}X_{25}X_{26}X_{27}X_{28}$$

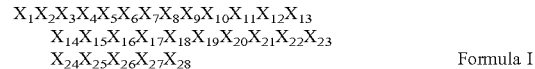

in the Formula I, $X_1$ to $X_{28}$ are each an amino acid residue, $X_1$ is W, L or Y, $X_2$ is E or T, $X_3$ is Q, A or S, $X_4$ is K, N or L, $X_5$ is I or L, $X_6$ is E, D, K, R or A, $X_7$ is E, D, K, R or A, $X_8$ is L or I, $X_9$ is L or I, $X_{10}$ is K, R, E, D or A, $X_{11}$ is K, R, E, D or A, $X_{12}$ is A or S, $X_{13}$ is E, D, K, R or A, $X_{14}$ is E, D, K, R or A, $X_{15}$ is Q, $X_{16}$ is Q, $X_{17}$ is K, R, E, D or A, $X_{18}$ is K, R, E, D or A, $X_{19}$ is N, $X_{20}$ is E or D, and $X_{21}$ is E, D, K, R or A, $X_{22}$ is E, D, K, R or A, $X_{23}$ is L or I, $X_{24}$ is K, R, E, D or A, $X_{25}$ is K, R, E, D or A, $X_{26}$ is L or I, $X_{27}$ is E or D, $X_{28}$ is K or R;

the P2 is a polypeptide obtained by deleting 1 to 4 amino acid residues at the amino-terminus of the P1 (i.e., 1 to 4 of the four amino acid residues of $X_1$, $X_2$, $X_3$ and $X_4$ in the Formula I);

the P3 is a polypeptide obtained by deleting 1 to 3 amino acid residues at the carboxyl-terminus of the P1 (i.e., 1 to 3 of the three amino acid residues of $X_{26}$, $X_{27}$ and $X_{28}$ in the Formula I);

the P4 is a polypeptide obtained by adding a cysteine residue to the carboxyl-terminus of the P1;

the P5 has a sequence as shown in the following Formula II, $$X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}X_{25}$$   Formula II in the Formula II, the definitions of $X_5$ to $X_{25}$ are same as those in the Formula I;

the polypeptide having an antiviral activity against any one virus selected from the group consisting of the following v1-v7:

v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

It has been experimentally proved that the above P5 is a core sequence of the lipopeptide of the present invention. The antiviral activity of the core sequence is effectively improved by adding 1 to 4 amino acid residues at the N-terminus thereof and/or adding 1-3 amino acid residues at the C-terminus thereof.

In the above lipopeptide, a pharmaceutically acceptable salt thereof, a derivative thereof, the lipopeptide has higher antiviral activity than LP-19 and/or T-20 and/or C34-Chol.

The P1 has a sequence as shown in the following sequence:

$$X_1X_2X_3X_4IEELX_9KKX_{12}EEQQKKNEEELKKLEK;$$

the P2 is P2-1, P2-2, P2-3 or P2-4, wherein
the P2-1 has a sequence as shown in the following sequence:

$$X_2X_3X_4IEELX_9KKX_{12}EEQQKKNEEELKKLEK;$$

the P2-2 has a sequence as shown in the following sequence:

$$X_3X_4IEELX_9KKX_{12}EEQQKKNEEELKKLEK;$$

the P2-3 has a sequence as shown in the following sequence:

$$X_4IEELX_9KKX_{12}EEQQKKNEEELKKLEK;$$

the P2-4 has a sequence as shown in the following sequence:

$$IEELX_9KKX_{12}EEQQKKNEEELKKLEK;$$

the P3 has a sequence as shown in the following sequence:

$$X_1X_2X_3X_4IEELX_9KKX_{12}EEQQKKNEEELKK;$$

the P4 has a sequence as shown in the following sequence:

$$X_1X_2X_3X_4IEELX_9KKX_{12}EEQQKKNEEELKKLEKC;$$

in the P1, P2-1, P2-2, P2-3, P2-4, P3 and P4, the definitions of $X_1$, $X_2$, $X_3$, $X_4$, $X_9$ and $X_{12}$ are same as those in the Formula I.

In the above lipopeptide, a pharmaceutically acceptable salt thereof, a derivative thereof, except for $X_n$ (n is a natural number in any of 1 to 28) in the sequences of the polypeptide, each of the capital letters is an abbreviation of an amino acid, wherein the abbreviation of an amino acid has the meanings well known in the art, for example: Y is tyrosine, T is threonine, S is serine, L is leucine, I is isoleucine, E is glutamic acid, K is lysine, Q is glutamine, N is asparagine, A is alanine, and W is tryptophan. All of the amino acids in the sequences of the polypeptides may be L-form amino acids, and one or more (e.g., 2-5, 2-4, or 2-3) amino acids of which may also be replaced with D-form amino acid(s), artificially modified amino acid(s), rare amino acid(s) present in nature, etc., to improve the bioavailability, stability, and/or antiviral activity of the polypeptides, wherein the D-form amino acid refers to an amino acid corresponding to a L-form amino acid constituting a protein; the artificially modified amino acid refers to a common L-form amino acid which constitutes a protein and is modified by means of methylation, phosphorylation or the like; and the rare amino acid present in nature includes an uncommon amino acids constituting a protein and an amino acid not constituting a protein, for example, 5-hydroxylysine, methylhistidine, gamma aminobutyric acid, homoserine, etc.

In the above lipopeptide, a pharmaceutically acceptable salt thereof, or a derivative thereof, the P1 is P-80/84/85/52, P-87/51 or P50, wherein the P-80/84/85/52 is a polypeptide represented by the sequence of SEQ ID NO: 1 in the sequence listing (i.e., the polypeptide represented by amino acid residues at the positions of 1 to 28 of the LP-80, LP-84, LP-85 or LP-52 in FIG. 2), the P-87/51 is a polypeptide represented by the sequence of SEQ ID NO: 2 in the sequence listing (i.e., the polypeptide represented by amino acid residues at the positions of 1 to 28 of the LP-87 or LP-51 in FIG. 2), and the P50 is a polypeptide represented by the sequence of SEQ ID NO: 3 in the sequence listing (i.e., the polypeptide represented by amino acid residues at positions of 1-28 of the LP-50 in FIG. 2). The P2-1 is P-88/62, wherein the P-88/62 is a polypeptide represented by the sequence of SEQ ID NO: 4 in the sequence listing (i.e., the polypeptide represented by amino acid residues at the positions of 1 to 27 of the LP-88 or LP-62 in FIG. 2). The P2-2 is P63 or P60, wherein the P63 is a polypeptide represented by the sequence of SEQ ID NO: 5 in the sequence listing (i.e., the polypeptide represented by amino acid residues at the positions of 1 to 26 of the LP-63 in FIG. 2), and the P60 is a polypeptide represented by the sequence of SEQ ID NO: 6 in the sequence listing (i.e., the polypeptide represented by amino acid residues at the positions of 1 to 26 of the LP-60 in FIG. 2). The P2-3 is P-89/64, wherein the P-89/64 is a polypeptide represented by the sequence of SEQ ID NO: 7 in the sequence listing (i.e., the polypeptide represented by amino acid residues at the positions of 1 to 25 of the LP-89 or LP-64 in FIG. 2). The P2-4 is P-90/65 or P61, wherein the P-90/65 is a polypeptide represented by the sequence of SEQ ID NO: 8 in the sequence listing (i.e., the polypeptide represented by amino acid residues at the positions of 1 to 24 of the LP-90 or LP-65 in FIG. 2); and the P61 a polypeptide represented by the sequence of SEQ ID NO: 9 in the sequence listing (i.e., the polypeptide represented by amino acid residues at the positions of 1 to 24 of the LP-61 in FIG. 2). The P3 is P-91/55, wherein the P-91/55 is a polypeptide represented by the sequence of SEQ ID NO: 10 in the sequence listing (i.e., the polypeptide represented by amino acid residues at the positions of 1 to 25 of the LP-91 or LP-55 in FIG. 2). The P4 is P83 or P86, wherein the P83 is a polypeptide represented by the sequence of SEQ ID NO: 11 in the sequence listing (i.e., the polypeptide represented by amino acid residues at the positions of 1 to 29 of the LP-83 in FIG. 2), and the P86 is a polypeptide represented by the sequence of SEQ ID NO: 12 in the sequence listing (i.e., the polypeptide represented by amino acid residues at the positions of 1 to 29 of the LP-86 in FIG. 2).

In the above lipopeptide, a pharmaceutically acceptable salt thereof, a derivative thereof, the lipophilic compound may be a fatty acid containing 8 to 20 carbon atoms, cholesterol (Chol), dihydrosphingosine (DHS), vitamin E (tocopherol, Toc), etc.

In the above lipopeptide, a pharmaceutically acceptable salt thereof, or a derivative thereof, the fatty acid containing 8 to 20 carbon atoms may be palmitic acid (also known as hexadecanoic acid) (C16) or stearic acid (C18).

In the above lipopeptide, a pharmaceutically acceptable salt thereof, or a derivative thereof, the lipophilic compound may be linked to side chain of the terminal amino acid or may be directly linked to peptide chain. The modification with a fatty acid, dihydrosphingosine or vitamin E as a lipophilic compound linked to the C-terminus may be accomplished by an amidation reaction thereof with the side chain amino group of lysine (Lys) at the end of the polypeptide, and the modification with cholesterol may be accomplished by grafting the cholesterol to the polypeptide chain by means of a thioether-forming reaction with a high chemical selectivity which is carried out between a side chain thiol group of cysteine (Cys) at the end of the polypeptide and cholesteryl bromoacetate.

In the above lipopeptide, a pharmaceutically acceptable salt thereof, or a derivative thereof, the lipopeptide may be any one of the following 12 lipopeptides LP-80/84/85/52, LP-90/65, LP-87/51, LP-88/62, LP-50, LP-83, LP-91/55, LP-86, LP-63, LP-89/64, LP-60 and LP-61.

The LP-80/84/85/52 is LP-80/84/85/52a or LP-80/84/85/52b, wherein the LP-80/84/85/52a is formed by linking the P-80/84/85/52 to a lipophilic compound linked to the carboxyl-terminus of the P-80/84/85/52; the LP-80/84/85/52b is formed by linking the LP-80/84/85/52a to the terminal protecting group; in the LP-80/84/85/52a and LP-80/84/85/52b, the lipophilic compound is stearic acid, dihydrosphingosine, vitamin E or palmitic acid.

The LP-90/65 is LP-90/65a or LP-90/65b, wherein the LP-90/65a is formed by linking the P-90/65 to a lipophilic compound linked to the carboxyl-terminus of the P-90/65; the LP-90/65b is formed by linking the LP-90/65a to the terminal protecting group; in the LP-90/65a and LP-90/65b, the lipophilic compound is stearic acid or palmitic acid.

The LP-87/51 is LP-87/51a or LP-87/51b, wherein the LP-87/51a is formed by linking the P-87/51 to a lipophilic compound linked to the carboxyl-terminus of the P-87/51; the LP-87/51b is formed by linking the LP-87/51a to the terminal protecting group; in the LP-87/51a and LP-87/51b, the lipophilic compound is dihydrosphingosine or palmitic acid.

The LP-88/62 is LP-88/62a or LP-88/62b, wherein the LP-88/62a is formed by linking the P-88/62 to a lipophilic compound linked to the carboxyl-terminus of the P-88/62; the LP-88/62b is formed by linking the LP-88/62a to the terminal protecting group; in the LP-88/62a and LP-88/62b, the lipophilic compound is stearic acid or palmitic acid.

The LP-50 is LP-50a or LP-50b, wherein the LP-50a is formed by linking the P-50 to palmitic acid linked to the carboxyl-terminus of the P-50; the LP-50b is formed by linking the LP-50a to the terminal protecting group.

The LP-83 is LP-83a or LP-83b, wherein the LP-83a is formed by linking the P-83 to cholesterol linked to the carboxyl-terminus of the P-83; the LP-83b is formed by linking the LP-83a to the terminal protecting group.

The LP-91/55 is LP-91/55a or LP-91/55b, wherein the LP-91/55a is formed by linking the P-91/55 to a lipophilic compound linked to the carboxyl-terminus of the P-91/55; the LP-91/55b is formed by linking the LP-91/55a to the terminal protecting group; in the LP-91/55a and LP-91/55b, the lipophilic compound is stearic acid or palmitic acid.

The LP-86 is LP-86a or LP-86b, wherein the LP-86a is formed by linking the P-86 to cholesterol linked to the carboxyl-terminus of the P-86; the LP-86b is formed by linking the LP-86a to the terminal protecting group. The LP-63 is LP-63a or LP-63b, wherein the LP-63a is formed by linking the P-63 to palmitic acid linked to the carboxyl-terminus of the P-63; the LP-63b is formed by linking the LP-63a to the terminal protecting group. The LP-89/64 is LP-89/64a or LP-89/64b, wherein the LP-89/64a is formed by linking the P-89/64 to a lipophilic compound linked to the carboxyl-terminus of the P-89/64; the LP-89/64b is formed by linking the LP-89/64a to the terminal protecting group; in the LP-89/64a and LP-89/64b, the lipophilic compound is stearic acid or palmitic acid.

The LP-60 is LP-60a or LP-60b, wherein the LP-60a is formed by linking the P-60 to palmitic acid linked to the carboxyl-terminus of the P-60; the LP-60b is formed by linking the LP-60a to the terminal protecting group. The LP-61 is LP-61a or LP-61b, wherein the LP-61a is formed by linking the P-61 to palmitic acid linked to the carboxyl-terminus of the P-61; the LP-61b is formed by linking the LP-61a to the terminal protecting group.

In the above lipopeptide, a pharmaceutically acceptable salt thereof, or a derivative thereof, the lipopeptide of the present invention may contain a N-terminal protecting group at the amino-terminus, wherein the N-terminal protecting group may be any one selected from the group consisting of acetyl, amino, maleoyl, succinyl, tert-butoxycarbonyl, benzyloxy, other hydrophobic group and macromolecular carrier group; the lipopeptide of the present invention may contain a C-terminal protecting group at the carboxyl-terminus, wherein the C-terminal protecting group may be any one selected from the group consisting of amino, amide, carboxyl, tert-butoxycarbonyl, other hydrophobic group and macromolecular carrier group.

Any one polypeptide selected from the group consisting of the above P1 to P4, a pharmaceutically acceptable salt thereof, or a derivative thereof is also within the scope of the present invention.

The derivative of the polypeptide may specifically be at least one selected from the group consisting of the following 1) to 5):

1) a derivative obtained by linking a N-terminal protecting group to the amino-terminus of the polypeptide and/or by linking a C-terminal protecting group to the carboxyl-terminus of the polypeptide;

2) a derivative obtained by linking an oligopeptide or a lipophilic compound to the carboxyl-terminus of the polypeptide;

3) a derivative obtained by linking an oligopeptide or a lipophilic compound to the amino-terminus of the polypeptide;

4) a derivative obtained by linking an oligopeptide or a lipophilic compound to the both carboxyl-terminus and amino-terminus of the polypeptide; and 5) a derivative obtained by modifying the polypeptide with a protein, a polyethylene glycol or a maleimide.

Multimer of PM1 or PM2 is also within the scope of the present invention, wherein the PM1 is a multimer formed by the lipopeptide, a pharmaceutically acceptable salt thereof, or a derivative thereof; and the PM2 is a multimer formed by the polypeptide, a pharmaceutically acceptable salt thereof, or a derivative thereof.

The following composition is also within the scope of the present invention. A composition comprising C1) and C2), wherein the C1) is C11), C12) or/and C13), the C11) is the lipopeptide, a derivative, or a pharmaceutically acceptable salt thereof, the C12) is the polypeptide, a derivative thereof, or a pharmaceutically acceptable salt thereof, the C13) is the multimer;

the C2) is a pharmaceutically acceptable carrier or adjuvant;

the composition has at least one function of the following functions F1)-F5):

F1) having activity against virus;
F2) treating and/or preventing and/or adjunctively treating a disease caused by a virus infection;
F3) inhibiting fusion of virus and cell;
F4) inhibiting entry of virus into cell; and
F5) inhibiting replication of virus;

in the F1)-F5), the virus is any one virus selected from the group consisting of the following v1-v7:

v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

Use of the C11), C12), C13) and/or C14) in the manufacture of at least one product selected from the group consisting of E1)-E5) is also within the scope of the present invention, wherein the C14) is the composition;
the E1) is an product against virus such as a drug or a vaccine;
the E2) is a product, such as a drug or a vaccine, for treating and/or preventing and/or adjunctively treating a disease caused by a virus infection, such as AIDS;
the E3) is a product for inhibiting fusion of virus and cell, such as a drug or a vaccine;
the E4) is a product for inhibiting entry of virus into cell, such as a drug or a vaccine; and
the E5) is a product for inhibiting replication of virus, such as a drug or a vaccine;

in the E1)-E5), the virus is any one virus selected from the group consisting of the following v1-v7:

v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

The present invention provides a pharmaceutical compound.

The pharmaceutical compound provided by the present invention is the C11), the C12) or the C13).

In the above pharmaceutical compound, the pharmaceutical compound has at least one of the following uses U1)-U5):

U1) use for being against virus
U2) use for treating and/or preventing and/or adjunctively treating a disease caused by a virus infection (such as AIDS);
U3) use for inhibiting fusion of virus and cell;
U4) use for inhibiting entry of virus into cell; and
U5) use for inhibiting replication of virus;

in the U1)-U5), the virus is any one virus selected from the group consisting of the following v1-v7:

v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

A method of treating or/and preventing an infection caused by a virus in an animal is also within the scope of protection of the present invention.

The method of treating or/and preventing an infection caused by a virus in an animal comprises administering to a subject animal the C11), the C12), the C13) or/and C14) to inhibit viral infection in the animal, wherein the C14) is the composition; and
the virus is any one virus selected from the group consisting of the following v1-v7:

v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

The pharmaceutically acceptable salt of the lipopeptide and the pharmaceutically acceptable salt of the polypeptide according to the present invention, include acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate, embonate, estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, triethiodide, lactate, and valerate etc. Depending on the use, the pharmaceutically acceptable salt may be formed from cations such as sodium, potassium, aluminum, calcium, lithium, magnesium, zinc, and bismuth, or may be formed from a base such as ammonia, ethylenediamine, N-methyl-glutamine, lysine, arginine, ornithine, choline, N,N'-dibenzylethylene-diamine, chloroprocaine, diethanolamine, procaine, diethylamine, piperazine, tris(hydroxymethylaminomethane) and tetramethylammonium hydroxide. These salts may be prepared by standard methods, for example, by a reaction of a free acid with an organic or inorganic base. In the presence of a basic group (e.g., an amino group), an acid salt such as a hydrochloride, a hydrobromide, an acetate, a pamoate or the like may be used as a form of a drug; in the presence of an acidic group (e.g., —COOH) or an alcohol group, a pharmaceutically acceptable ester such as an acetate, a maleate, a pivaloyloxymethyl, and an ester known in the literatures for improving solubility and hydrolyzability may be used as a form of sustained release drug or prodrug.

In the present invention, the antiviral activity may also be referred to as inhibitory activity against virus, specifically, inhibiting fusion of virus and cell and/or inhibiting entry of virus into cell and/or inhibiting replication of virus. Significantly long-acting antiviral effect exhibits in non-human primates (monkeys).

The lipopeptide or polypeptide, the derivative thereof, or the pharmaceutically acceptable salt thereof, the multimer, the composition or the pharmaceutical compound provided by the present invention, may be used for treating HIV (HIV-1 and/or HIV-2) infection and/or SIV infection, including various stages of HIV infection and/or SIV infection, such as the onset stage, sympathetic stage and asymptomatic stages of AIDS. The lipopeptide or polypeptide, the derivative thereof, or the pharmaceutically acceptable salt thereof, the multimer, the composition or the pharmaceutical compound provided by the present invention, may also be used for preventing HIV (HIV-1 and/or HIV-2) infection and/or SIV infection, including pre-exposure or after suspicious exposure, such as blood transfusion, organ transplantation, body fluid exchange, bite, accidental needle sticks or exposure to the patient's blood during surgery.

In practice, the lipopeptide or polypeptide, the derivative thereof, or the pharmaceutically acceptable salt thereof, the multimer, the composition, or the pharmaceutical compound according to the present invention may be administered to a patient as a medicament either directly or in admixture with a suitable carrier or excipient for the purpose of treating and/or preventing HIV infection. The material of the carrier herein includes, but are not limited to, water-soluble carrier material (e.g., polyethylene glycol, polyvinylpyrrolidone, organic acid, etc.), poorly soluble carrier material (e.g., ethyl cellulose, cholesterol stearate, etc.), enteric soluble carrier material (e.g., cellulose acetate phthalate, carboxymethyl cellulose, etc.), wherein the water-soluble carrier material is preferred. By using these materials, various preparation forms can be prepared, including but not limited to tablet, capsule, dripping pill, aerosol, pill, powder, solution, suspension, emulsion, granule, liposome, transdermal agent, buccal tablet, suppository, freeze-dried powder for injection and the like, wherein the suppository may be a vaginal suppository, a vaginal ring, or an ointment, cream or gel suitable for vaginal application. The preparation form may be a common preparation, a sustained release preparation, a controlled release preparation and various particle delivery systems. In order to formulate a unit preparation form into a tablet, a wide variety of carriers known in the art may be used. Examples of carriers are, for example, diluent and absorbent, such as starch, dextrin, calcium sulfate, lactose, mannitol, sucrose, sodium chloride, glucose, urea, calcium carbonate, kaolin, microcrystalline cellulose, and aluminum silicate; wetting agent and binder, such as water, glycerol, polyethylene glycol, ethanol, propanol, starch slurry, dextrin, syrup, honey, glucose solution, gum arabic, gelatin paste, sodium carboxymethylcellulose, shellac, methylcellulose, potassium phosphate, and polyvinyl pyrrolidone; disintegrant, such as dried starch, alginate, agar powder, brown algae starch, sodium bicarbonate and citric acid, calcium carbonate, polyoxyethylene, sorbitol fatty acid ester, sodium dodecylsulfate, methyl cellulose, and ethyl cellulose; disintegration inhibitor, such as sucrose, glyceryl tristearate, cocoa butter, hydrogenated oil and the like; absorption promoters, such as quaternary ammonium salts, and sodium lauryl sulfate; lubricant, such as talc, silica, corn starch, stearate, boric acid, liquid paraffin, and polyethylene glycol. The tablet may also be further formulated into a coated tablet, such as sugar-coated tablet, film-coated tablet, enteric-coated tablet, or double or multiple layer tablet. In order to formulate a unit preparation form into a pill, a wide variety of carriers known in the art may be used. Examples of the carrier are, for example, diluent and absorbent, such as glucose, lactose, starch, cocoa butter, hydrogenated vegetable oil, polyvinyl pyrrolidone, Gelucire, kaolin, and talc; binder, such as gum arabic, tragacanth, gelatin, ethanol, honey, liquid sugar, rice paste, and flour paste; disintegrant, such as agar powder, dried starch, alginate, sodium dodecyl sulfate, methyl cellulose, and ethyl cellulose. In order to formulate a unit preparation form into a suppository, a wide variety of carriers known in the art may be used. Examples of the carrier are, for example, polyethylene glycol, lecithin, cocoa butter, higher alcohol, higher alcohol ester, gelatin, and semi-synthetic glyceride. In order to formulate a unit preparation form into a preparation for injection such as a solution, an emulsion, a freeze-dried powder and a suspension, all conventional diluents may be used, for example, water, ethanol, polyethylene glycol, 1,3-propanediol, ethoxylated isostearyl alcohol, polyoxylated isostearyl alcohol, polyoxyethylene sorbitan fatty acid ester, etc. In addition, in order to prepare an isotonic injection, to a preparation for injection, sodium chloride, glucose, or glycerin in a suitable amount may be added, and conventional cosolvent, buffer, pH-adjusting agent may also be added. Besides, if required, coloring agent, preservative, perfume, flavor, sweeting agent, and other material may optionally be added to the pharmaceutical preparation.

The above preparation forms may be administered by injection including subcutaneous injection, intravenous injection, intramuscular injection and intraperitoneal injection, intracisternal injection or infusion etc., intraluminal administration such as transrectal, vaginal and sublingual administration, respiratory administration such as nasal administration; and mucosal administration. Among the above administration routes, administration by injection is preferred, and a preferred injection route is a subcutaneous injection.

The administration dose of the lipopeptide or polypeptide, the derivative thereof, the pharmaceutically acceptable salt thereof, the multimer, the composition, or the pharmaceutical compound of the present invention depends on various factors, for example, the nature and severity of a disease to be prevented or treated, the gender, age, weight and individual response of a patient or animal, a particular active ingredient used, an administration route, and an administration frequency etc. The above dose may be administered in a single-unit dosage form or multiple- (e.g., two, three or four) unit dosage forms.

A specific therapeutically effective dose level for any particular patient will depend on various factors, including disorder being treated and the severity thereof; the activity of particular active ingredient used; a particular composition used; the age, weight, general health, gender and diet of a patient; an administration time, an administration route and an excretion rate of a particular active ingredient used; a duration of treatment; a drug used together with the particular active ingredient used in combination or simultaneously; and similar factors well known in the medical field. For example, it is common practice in the art to start with a dosage of an active ingredient at a level below that required to achieve a desired therapeutic effect, and to gradually increase the dosage until the desired effect is achieved. In general, the lipopeptide, the derivative thereof, or the pharmaceutically acceptable salt thereof, the multimer, the composition or the pharmaceutical compound of the present invention may be administered to a mammal, particularly a human, in a dosage of between 0.001 and 1000 mg/kg body weight/day, such as between 0.01 and 100 mg/kg body weight/day, and such as between 0.1 and 10 mg/kg body weight/day and at an frequency of 1-2 times/day, 1 time/2 days, 1 time/3 days, 1 time/4 days, 1 time/5 days, 1 time/6 days or 1 time/7 days, preferably 1 time/1-2 days or 1-2 times/week.

The lipopeptide or polypeptide, the derivative thereof, or the pharmaceutically acceptable salt thereof, the multimer, the composition, or the pharmaceutical compound of the present invention may be directly used alone for the treatment or prevention of HIV infected patient, or may be used in combination with one or more anti-HIV drugs, either simultaneously or at intervals to achieve an improved overall therapeutic effect. The anti-HIV drugs include, but are not limited to, reverse transcriptase inhibitors, protease inhibitors, entry inhibitors, integration inhibitors, maturation inhibitors, and the like. The above reverse transcriptase inhibitor may be one or more of nucleoside reverse transcriptase inhibitors, e.g., Zidovudine (AZT), Lamivudine (3TC), Didanosine (ddI), Zalcitabine (ddC), Stavudine (d4T), Tenofovir (TDF), Abacavir (ABC), Emtricitabine (FTC), etc., and may also be one or more of non-nucleoside reverse transcriptase inhibitors, e.g., Nevirapine (NVP), Efavirenz (EFV), Delavirdine (DLV), Etravirine (ETR), etc. The above protease inhibitors may be one or more inhibitors selected from the group consisting of Saquinavir (SQV-HGC), Indinavir (IDV), Ritonavir (RTV), Amprenavir (APV), Lopinavir and Ritonavir (LPV/RTV), Nelfinavir (NFV), Fosamprenavir calcium (FPV), Reyataz (ATV), Prezista and the like. The above integration inhibitors may be one or more inhibitors selected from the group consisting of Raltegravir, Dolutegravir, Elvitegravi and the like. The above invasion inhibitors may be one or more of Maraviroc, T-20, TAK-779, T2635, VIRIP (VIR-576), Sifuvirtide, Albuvirtide, soluble CD4 protein and analog thereof, antibody against the coreceptor CCR5 (e.g., PRO140), monoclonal antibody against gp120/gp41 (e.g., VRCO1 and 10E8), monoclonal antibody against the receptor CD4 (e.g., TNX-355) and the like.

The strategy for designing the lipopeptide of the present invention is that: the C-terminal TRM sequence of 8 amino acids (WASLWNWF) of the T-20 polypeptide is substituted with a lipophilic compound, such as a long chain fatty acid (e.g., palmitic acid or stearic acid), cholesterol, dihydrosphingosine or vitamin E to produce a lipopeptide comprising a polypeptide sequence corresponding to the first 28 amino acids of T-20, i.e., corresponding to amino acids at positions of 127-154 of the gp41 from HIV-1 strain HXB 2; further, the EE**KK amino acid residues which contribute to the formation of the ion pairs are introduced by mutating the amino acid at the non-NHR binding surface (i.e., the corresponding amino acid at positions of b, c, and f, g) of the polypeptide sequence, and the corresponding amino acid residues of HIV-2 and/or SIV are introduced by mutating the amino acid at the NHR binding surface (i.e., the corresponding amino acid at positions of a and d) of the polypeptide sequence. Further, the C-terminal and/or N-terminal sequence of the produced lipopeptide is truncated to produce a set of lipopeptides having less than 28 amino acids, i.e., containing 24 to 27 amino acids, and the sequence corresponding to amino acids at positions of 5 to 25 of the T-20, i.e., corresponding to amino acids at positions of 131 to 151 of gp41 from HXB2 strain, is determined to be the core sequence (i.e., the P5 sequence) of the potent HIV inhibitors of the present invention. The polypeptides of the present patent have an outstanding sequence structural characteristic, have a chemical medication with a lipophilic compound linked to the C-terminus, and have a remarkably enhanced ability to bind to a target sequence, an extremely strong inhibitory activity against HIV (HIV-1 and/or HIV-2) and/or SIV, and highly potent ability to inhibit cell-cell fusion, virus entry and infection medicated by HIV envelope protein (Env). The anti-HIV activity of the lipopeptide of the present invention is higher than that of T-20 by several thousands of times or even tens of thousands of times, and is also significantly higher than that of the anti-HIV lipopeptide with a higher activity such as C34-Chol, LP-11, LP-19 and the like. Meantime, the lipopeptide of the present invention has many advantages, such as stable long-acting effect, easy synthesis and low cost. The lipopeptide of the present invention has very strong inhibitory activity against various HIV-1 subtypes (such as A, B, C, A/E and B/C subtypes), T-20 resistant strains, HIV-2 strains and Simian Immunodeficiency Virus (SIV).

DESCRIPTION OF THE FIGURES

FIG. 2 shows the sequence structures of HIV membrane fusion inhibitors and their antiviral activity. Wherein, the TRM sequence of T-20 is indicated in italics, the M-T hook and PBD sequences are underlined. In the polypeptide linker arm, the AHX refers to 6-aminocaproic acid, AEEA means 8-amino-3,6-dioxaoctanoic acid, PEG4, PEG8 and PEG12 refer to polyethylene glycols with different lengths, wherein PEG4 is Fmoc-NH-PEG4-CH$_2$CH$_2$COOH, PEG 8 is Fmoc-NH-PEG8-CH$_2$CH$_2$COOH, and PEG 12 is Fmoc-NH-PEG12-CH$_2$CH$_2$COOH. C16 represents palmitic acid, C18 represents stearic acid, Chol represents cholesterol, DHS represents dihydrosphingosine, Toc represents vitamin E, C12 represents dodecanoic acid (lauric acid), and C8 represents octanoic acid (caprylic acid). The NL4-3 pseudovirus is a mutant of gp41 with D36G. The experiment is repeated three times and the average IC$_{50}$ value is calculated. Some of the potent lipopeptides are marked in bold face. The "HXB2-cell fusion" represents the experimental results of inhibiting cell fusion mediated by an HIV-1, the "Entry of NL4-3" represents the experimental results of inhibiting cell entry mediated by an HIV-1 pseudovirus, and the "Replication of JRCSF" represents the results of inhibiting HIV-1 replication.

FIG. 3 shows the inhibitory effect of HIV membrane fusion inhibitors on various subtypes of HIV-1 strain. The experiment is repeated three times and the average $IC_{50}$ value is calculated.

In FIG. 5, A shows the antiviral activity in serum of macaque after injection of T-20; B shows the antiviral activity in serum of macaque after injection of LP-19; C shows the antiviral activity in serum of macaque after injection of LP-51; D shows the antiviral activity in serum of macaque after injection of LP-52; E shows the antiviral activity in serum of macaque after injection of LP-80; F shows the comparison result of antiviral activity of the inhibitors in serum.

FIG. 6 shows the results of circular dichroism analysis of the interaction between HIV membrane fusion inhibitors and NHR. The sequence structures of the inhibitors are the same as those in FIG. 2 of the present invention, wherein the potent lipopeptides of the present invention are marked in bold face. The inhibitors and the N39 polypeptide are dissolved in phosphate buffered saline (PBS) at pH 7.2 to arrive at a final concentration of 10 μM.

In FIG. 7, A shows the CD scanning results; B shows the temperature scanning results.

In FIG. 8, A and B show the CD scanning and temperature scanning results of the inhibitors at 10 μM, respectively; C and D show the CD scanning and temperature scanning results of the inhibitors at 20 μM, respectively; and E and F show the CD scanning and temperature scanning results of the inhibitors at 40 μM, respectively.

In FIG. 9, A shows the detection results of serum drug concentrations of LP-80 after administration; B shows the metabolic kinetic parameters of LP-80, wherein $T_{1/2}$ refers to the terminal half-life, $C_{max}$ refers to the concentration of peak, $T_{max}$ refers to the time to the peak, $AUC_{(0-216\ h)}$ refers to the area under curve (0-216 h), Vz refers to the apparent volume of distribution, CL refers to the clearance, MRT refers to the mean residence time, and $F_{abs}$ is absolute bioavailability.

OPTIMUM MODE FOR CARRYING OUT THE PRESENT INVENTION

Figure 1:
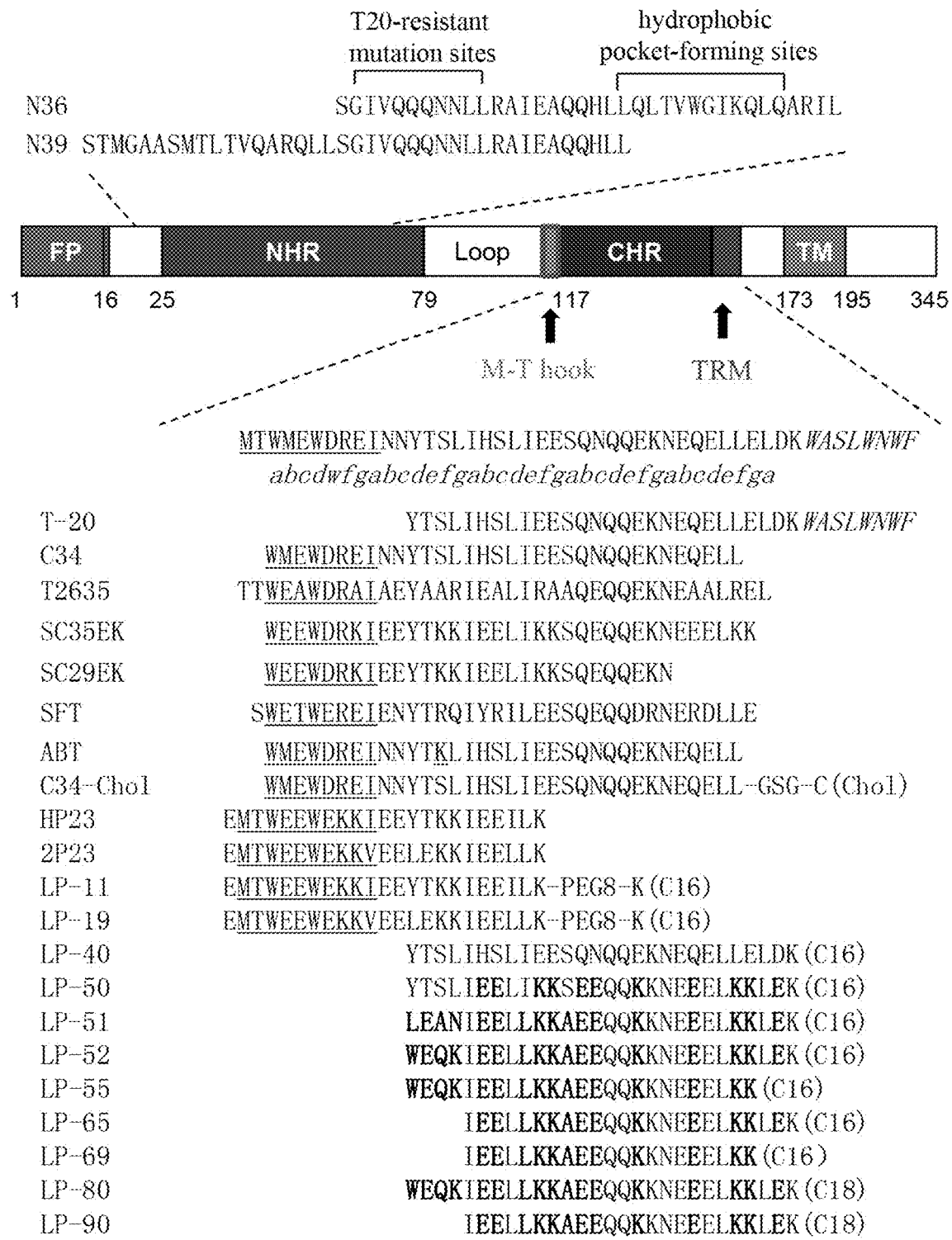
FIG. 1 shows the structure and function of the HIV fusion protein gp41 and a polypeptide-based membrane fusion inhibitor. Wherein, FP refers to a gp41 fusion peptide; NHR refers to an N-terminal repeat sequence; CHR refers to a C-terminal repeat sequence; and TM refers to a transmembrane region. The position indicated by the arrow is the "M-T hook" position or tryptophan-rich motif (TRM) position. The N36 and N39 sequences of NHR polypeptide are above the schematic diagram of the gp41, and T-20 resistant sites and hydrophobic pocket-forming sites are marked respectively, and the sequence of CHR and the sequence of a CHR sequence-based inhibitor are below the schematic diagram of gp41, where the M-T and PBD sequences are underlined, the TRM sequence is indicated in italics, and the mutated amino acids of the polypeptide sequences of the present invention are indicated in bold face. The amino acids of all polypeptides or lipopeptides in the figure have an acetylation modification at the amino-terminus (Ac-), and an amidation modification at the carboxyl-terminus (—NH$_2$).

The embodiments of the present invention will be described in detail below with reference to examples, but a person skilled in the art will understand that the following examples are only for illustrating the present invention and should not be construed as limiting the scope of the present invention. When the conditions are not indicated in the Examples, the Examples are carried out under the conventional conditions or the conditions recommended by the manufacturers. The reagents or instruments used herein, the manufacturers of which are not indicated, are the conventional products that are commercially available. The amino acids of all the polypeptides in the following examples are L-type amino acids.

Example 1 Preparation of Lipopeptides

The structural formula of the lipopeptides provided in this embodiment was: Ac—$X_1X_2X_3X_4X_5X_6X_7X_8X_9X_{10}X_{11}X_{12}X_{13}X_{14}X_{15}X_{21}X_{17}X_{18}X_{19}X_{20}X_{26}X_{27}X_{28}Z$—$NH_2$, wherein $X_1$-$X_{28}$ represented a polypeptide sequence corresponding to amino acids at positions of 127 to 154 of the sequence of gp41 from HIV-1 strain HXB2 (YTS-LIHSLIEESQNQQEKNEQELLELDK), wherein $X_1$ corresponded to Y at the position of 127, and $X_2$ corresponded to T at the position of 128, $X_3$ corresponded to S at the position of 129, . . . $X_{28}$ corresponded to K at the position of 154. A novel sequence obtained by a large number of mutations was a component of potent inhibitors. Representative peptides included LP-50, LP-51, LP-52, LP-80, LP-83, LP-84, LP-85, LP-86 and LP-87, etc. The definitions of $X_1$-$X_{28}$ were same as those in Formula I, Z was a lipophilic compound, Ac was an acetyl group, and $NH_2$ was an amino group.

In this example, the lipopeptides or polypeptides as shown in FIG. 2 were synthesized, wherein the amino-terminus of each lipopeptide or polypeptide was linked by an acetyl group as an amino terminal protecting group, and the carboxyl-terminus was linked by an amino group as a carboxyl terminal protecting group.

Wherein, the modification of the polypeptide with palmitic acid (palmitic acid-modified lipopeptides: LP-40, LP-41, LP-42, LP-43, LP-44, LP-45, LP-50, LP-51, LP-52, LP-53, LP-54, LP-55, LP-56, LP-57, LP-58, LP-59, LP-60, LP-61, LP-62, LP-63, LP-64, LP-65, LP-66, LP-67, LP-68, LP-69, LP-70, LP-71, LP-72, LP-73, LP-74, LP-75, LP-11, LP-19, C34-C16), stearic acid (stearic acid-modified lipopeptides: LP-80, LP-88, LP-89, LP-90, LP-91, LP-92), dihydrosphingosine (dihydrosphingosine-modified lipopeptides: LP-84, LP-87), vitamin E (vitamin E-modified lipopeptide: LP-85), dodecanoic acid (dodecanoic acid-modified lipopeptide: LP-81), and octanoic acid (octanoic acid-modified lipopeptide: LP-82), was carried out by an amidation reaction thereof with the side chain amino group of lysine (Lys) at the C-terminus of the polypeptide, please see the References 18 and 27 listed in the Background art. Below, the LP-52 and LP-80 were taken as examples to illustrate the synthesis of the above lipopeptides.

The used chemical reagents, such as Rink Amide MBHA resin, various Fmoc amino acids, palmitoyl chloride, stearoyl chloride, vitamin E succinate, D-erythro-dihydrosphingosine, N,N'-disuccinimidyl carbonate, N,N'-diisopropylcarbodiimide (DIC), 1-hydroxybenzotriazole (HOBt), trifluoroacetic acid (TFA), ethanedithiol (EDT), ninhydrin, hexahydropyridine (PIPE), phenol, N,N'-dimethylformamide (DMF), chromatographically pure acetonitrile, etc., all were purchased from major chemical reagent suppliers and were not further purified prior to use.

Synthesis of the polypeptide: a synthesis was carried out from the C-terminus to the N-terminus with Rink Amide MBHA resin (substitution constant of 0.34 mmol/g) as a starting material by using a manual Fmoc solid phase synthesis method. The Fmoc protecting group on the Rink resin was removed with 25% hexahydropyridine/DMF (volume ratio), and then the resin was grafted with 2 equivalents of Fmoc-Lys(Dde)-OH/HOBt/DIC to introduce a first amino acid residue at the C-terminus. Thereafter, the N-terminal Fmoc protecting group was removed with 25% hexahydropyridine/DMF (volume ratio) again to make the N-terminus to be a free amino group. The various amino acid residues were sequentially linked by the way. The used materials and amounts thereof were as follows: Fmoc-Glu(OtBu)-OH (3 eq), Fmoc-Leu-OH (3 eq), Fmoc-Lys(Boc)-OH (3 eq), Fmoc-Lys(Boc)-OH (3 eq), Fmoc-Leu-OH (3 eq), Fmoc-Glu(OtBu)-OH (3 eq), Fmoc-Glu(OtBu)-OH (3 eq), Fmoc-Glu(OtBu)-OH (3 eq), Fmoc-Asn (Trt)-OH (3 eq), Fmoc-Lys(Boc)-OH (3 eq), Fmoc-Lys(Boc)-OH (3 eq), Fmoc-Gln (Trt)-OH (3 eq), Fmoc-Gln(Trt)-OH (3 eq), Fmoc-Glu (OtBu)-OH (3 eq), Fmoc-Glu(OtBu)-OH (3 eq), Fmoc-Ala-OH (3 eq), Fmoc-Lys(Boc)-OH (3 eq), Fmoc-Lys(Boc)-OH (3 eq), Fmoc-Leu-OH (3 eq), Fmoc-Leu-OH (3 eq), Fmoc-Glu(OtBu)-OH (3 eq), Fmoc-Glu (OtBu)-OH (3 eq), Fmoc-Ile-OH (3 eq), Fmoc-Lys(Boc)-OH (3 eq), Fmoc-Gln(Trt)-OH (3 eq), Fmoc-Glu(OtBu)-OH (3 eq), Fmoc-Trp(Boc)-OH (3 eq). Finally, the N-terminus was end-capped by means of acetylation (3 equivalents of $Ac_2O$, 6 equivalents of diisopropylethylamine) to complete the synthesis of the main chain. The reaction time of each step was as follows: deprotection for 8 minutes, twice; grafting of ordinary amino acids for 60 minutes.

After each step of the above reaction, the resin was needed to be washed with DMF for six times or more, and the reaction was controlled by Kaiser Test. If the condensation reaction of an amino acid was incomplete, the condensation was repeated once again until a desired peptide segment of interest was obtained.

Modification of the polypeptide: the resin was treated with 2% hydrazine hydrate/DMF solution (volume ratio) to remove the side chain Dde protecting group of the C-terminal Lys, and then mixed with 3 equivalent of palmitoyl chloride or stearoyl chloride and 6 equivalent of diisopropyl ethylamine to carry out an amidation reaction with the side chain amino group of the C-terminal Lys (60 minutes), thereby achieving palmitoylation modification (LP-52) or stearoyl modification (LP-80) of the C-terminal Lys residue. The modification of polypeptide with dihydrosphingosine (LP-84, LP-87) was carried out by first adding N,N'-disuccinimidyl carbonate after the side chain Dde protecting group of Lys was removed, then dihydrosphingosine was added, and the reaction was carried out for 48 hours. The modification of the polypeptide with vitamin E (LP-85) was carried out by an amidation of the deprotected side chain amino group of the Lys directly with vitamin E succinate.

Cleavage and deprotection of the side chain: after the synthesis of a lipopeptide was completed, the resin was dried under vacuum. A cleavage reagent (trifluoroacetic acid:1,2-ethanedithiol:thioanisole:phenol:$H_2O$:triisopropylsilane=68.5:10:10:5:3.5:1, v/v) was added to the dried resin, and the cleavage was carried out at 30° C. for 3 hours, whereby a polypeptide of interest was cleaved from the resin and the side chain protecting group was removed. A filtration operation was carried out. The filtrate was added to a large amount of cold anhydrous diethyl ether to precipitate the polypeptide, then centrifuged, the polypeptide was washed with diethyl ether for several times, and dried to obtain a crude lipopeptide product.

Purification and characterization of the lipopeptide: the purification of the crude lipopeptide product was performed on a reversed-phase high performance liquid chromatograph by using a 100×250 mm column containing reversed-phase $C_{18}$ or $C_4$ silica gel with a particle size of 10 μm and with a pore diameter of 100 angstroms (Å). The chromatographic operating conditions: linear gradient elution was performed, wherein an eluent consisted of a mobile phase A and a mobile phase B, the mobile phase A was an aqueous solution containing 20 mM ammonium acetate (pH 4.5) and 5% acetonitrile, and the mobile phase B was an aqueous solution of 80% (volume percentage concentration) acetonitrile; the flow rate was 250 ml/min; and the ultraviolet detection wavelength was 220 nm. After the solvent was freeze-dried, a pure product of the polypeptide in a fluffy state was obtained, the chemical structure of which was characterized by MALDI-TOF mass spectrometry, and the purity of which was determined by an analytical high performance liquid chromatography (C18-10×250 mm, flow rate: 1 ml/min). The results showed that the synthesized lipopeptides had a purity of more than 95%.

A method for synthesizing cholesterol-modified lipopeptides (LP-83, LP-86, C34-Chol) was carried out with reference to Reference 18 and Reference 20 listed in the Background Art. First, cholesteryl bromoacetate was synthesized according to the technical route described in the literatures, and then grafted to a polypeptide chain by means of a highly chemically selective thioether-forming reaction which is carried out between the side chain thiol group of the C-terminal cysteine (Cys) of the polypeptide and the cholesteryl bromoacetate, that was, after a crude polypeptide product was synthesized in a conventional manner, it was dissolved in pure DMSO, 1 equivalent of cholesteryl bromoacetate dissolved in a small amount of trifluoroacetic acid (TFA) was added thereto, and then pure diisopropylethylamine (DIEA) was added to adjust pH to alkaline. The reaction was followed by RP-HPLC and was generally completed in 1 hour. The lipopeptide was purified and characterized as above, and the purity of the obtained lipopeptide was more than 95%.

Example 2 Identification of Potent HIV Membrane Fusion Inhibitors 2.1 Experimental Materials and Methods Each of the lipopeptides and polypeptides in FIG. 2 was used as a test substance, and the anti-viral activity thereof was identified by a cell fusion inhibition assay, a pseudovirus inhibition assay, and a virus replication inhibition assay according to the Reference 18 listed in the Background Art. The specific method was as follows.

HIV-1 mediated cell fusion inhibition assay: the effector cells (HL2/3 cells) and target cells (TZM-b1 cells) were provided by the AIDS Reagent Program of National Institutes of Health (NIH) (catalog numbers: 1294 and 8129, respectively). The both cells were adherent cells and were cultured in a DMEM cell culture medium containing ampicillin/streptomycin double antibiotics and 10% fetal bovine serum (FBS). The TZM-b1 was first added to a 96-well cell culture plate ($1\times10^4$ cells/well), and cultured overnight at 37° C. and 5% $CO_2$. The test substance was diluted with the DMEM cell culture medium by 3 folds and mixed with HL2/3 effector cells ($3\times10^4$ cells/well), then added to the TZM-b1 target cells, and further cultured for 6 hours to fully fuse. The activity of luciferase (relative fluorescence units, RLU) was then determined using a luciferase reporter gene kit from Promega company according to the instructions. The inhibition rate of each sample at each concentration was calculated, and the half effective inhibitory concentration ($IC_{50}$ value) was calculated using GraphPad Prism Software 2.01.

HIV-1 pseudovirus-mediated cell entry inhibition assay: basic steps included: (1) Preparation of HIV-1 pseudovirus: the 293T cells were co-transfected with a plasmid expressing the envelope protein (Env) of HIV-1 strain NL4-3 (i.e., a recombinant expression plasmid obtained by inserting the gene encoding the envelope protein (ENV) of the D36G mutant of the HIV-1 strain NL4-3 in the Table 2 of the Reference 14 listed in the Background Art into the vector pcDNA3.1(−)) and the HIV-1 backbone plasmid pSG3Δenv (provided by the AIDS Reagent Program of National Institutes of Health (NIH), catalog number: 11051) by using a cell transfection reagent, incubated in a cell incubator of 37° C. and 5% $CO_2$ for 6 hours, and then the medium was changed, and the cells were further incubated for 48 hours. The cell culture supernatant containing pseudovirus particles was pipetted and filtered with a 0.45 μm filter to collect the supernatant, then 20% fetal bovine serum (FBS) was added thereto, the final solution was transferred to a polypropylene tube, and stored at −80° C. for ready for use or directly subjected to virus titration. (2) Titration of HIV-1 pseudovirus: the viruses were diluted by 5 folds in a 96-well plate, and 4 replicate wells with 8 gradients were set to a final volume of 100 microliters. The TZM-b1 cells were trypsinized and counted, and the cells were diluted to $1\times10^5$ cells/ml with DMEM complete medium; 100 μl of cells dilution (containing 15 μg/ml DEAE-dextran) per well were added and cultured at 37° C. and 5% $CO_2$ for 48 hours. The 96-well plate was then taken from the cell culture incubator. The supernatant was discarded from the wells. To each well, 30 μl of a cell lysate was added, and after 10 minutes, 100 μl of a luciferase detection reagent was added. 100 μl of liquid was pipetted from each well and added to a corresponding 96-well white plate, and the luminescence values were read by a microplate photometer. The virus titer was calculated by the Reed-Muench method. (3) Antiviral activity assay: the test substance was dissolved in DMSO and diluted with a cell culture solution by 3 folds, and placed in a 96-well plate at a final volume of 50 pt. 50 μl of a DMEM medium was used in place of the test substance as a negative control. To each well, 100 μl of TZM-b1 target cells solution (containing 15 μg/ml DEAE-dextran) at a concentration of $1\times10^5$ cells/ml was added, and then 50 μl (corresponding to 100 $TCID_{50}$ per well) of the HIV-1 pseudovirus obtained above was added. After incubation at 37° C. and 5% $CO_2$ for 48 hours, the relative light units (RLU) of each well were determined by using a luciferase detection reagent (Promega). Inhibition rate (%) and $IC_{50}$ value were calculated.

HIV-1 replication inhibition assay: the molecular cloning plasmid pYK-JRCSF encoding the HIV-1 strain JRCSF was provided by the AIDS Reagent Program of NIH (catalog number: 2708). 293T cells were transfected with the pYK-JRCSF by using a transfection reagent, and incubated in a cell incubator at 37° C. and 5% $CO_2$ for 6 hours; then the medium was changed, and the cells were further incubated for 48 hours. The cell culture supernatant containing the JRCSF viral particles was pipetted gently and filtered with a 0.45 μm filter to collect the supernatant, then 20% fetal bovine serum (FBS) was added thereto, and the final solution was transferred to a polypropylene tube, and stored at −80° C. for ready for use or directly subjected to virus titration. The virus titration was same as the above titration of HIV-1 pseudovirus. In order to detect the antiviral activity, the test substance was dissolved in DMSO and diluted with a cell culture solution by 3 folds, and placed in a 96-well plate at a final volume of 50 μL. 50 μL of a DMEM medium was used in place of the test substance as a negative control. To each well, 100 μl of TZM-b1 target cells solution (having $10^5$ cells/ml and containing 15 μg/ml DEAE-dextran) was added, and then 50 μl (100 $TCID_{50}$ per well) of the viruses obtained above was added. After incubation at 37° C. and 5% $CO_2$ for 48 hours, the relative light units (RLU) of each well were determined using a luciferase detection reagent (Promega). Inhibition rate (%) and $IC_{50}$ value were calculated.

2.2 Experimental Results and Analysis 2.2.1 the T-20-Based Lipopeptide (LP-40) had a Strong Antiviral Activity.

In order to screen and identify potent HIV membrane fusion inhibitors, the present invention had developed a new method in which a polypeptide drug T-20 that does not contain the NHR pocket-binding domain (PBD) was used as a design template. The inhibitory activity of an inhibitor against HIV-1 mediated cell fusion, pseudovirus entry and virus replication was evaluated using three antiviral assays (FIG. 2). First, by directly deleting the 8 amino acids at the C-terminus of the T-20, a polypeptide T20-TRM that does not contain the TRM motif was synthesized and found to have no significant antiviral activity at a high concentration of 2000 nM, which demonstrated an important role of TRM in the function of the T-20. Further, the lipopeptide LP-40 was synthesized by replacing the TRM of T-20 with palmitic acid (C16). It was surprisingly found that LP-40 had a significantly improved antiviral activity as compared to T-20, and that its inhibitory activity against HXB2-mediated cell fusion, NL4-3 pseudovirus entry and JRCSF replication was as about 59, 21 and 18 folds as that of T-20, respectively, which demonstrated that substitution of a lipophilic compound for TRM of T-20 could significantly improve the antiviral activity of the polypeptide, and which could be an important strategy for designing a HIV membrane fusion inhibitor.

2.2.2 Addition of a Linker Arm Resulted in Significant Reduction of Antiviral Activity of the LP-40.

The present inventors had previously designed a set of highly active anti-HIV lipopeptides based on modification of a short peptide (HP23 or 2P23) targeting the NHR pocket, and found that directly linking a lipid compound C16, cholesterol and dihydrosphingosine to the C-terminus of the polypeptide resulted in a significant decrease in the anti-HIV activity of the polypeptide, whereas the introduction of a linker arm between the polypeptide sequence and the compound modifier resulted in a significantly increase in the activity of the polypeptide, and the antiviral activity was increased with an increase in length of the linker arm (please see the References 18 and 30 listed in the Background Art). The finally designed high-activity lipopeptides such as LP-11 and LP-19 had a longer PEG8 linker arm, suggesting that the addition of a linker arm facilitated lipopeptides to overcome steric hindrance to produce function. In order to further improve the activity of LP-40, five lipopeptides of LP-41, LP-42, LP-43, LP-44 and LP-45 were designed and synthesized, which were respectively added with AHX, AEEA, PEG4, PEG8 and PEG12 as a linker arm (FIG. 2). Surprisingly, the addition of the linker arm resulted in a significant decrease in the activity of the lipopeptides, and the decrease in activity was more significant with an increase in length of the linker arm, which were exactly opposite to the results for the HP23- and 2P23-based lipopeptides. These results suggested that HP23- and 2P23-based lipopeptides had different mechanisms of action as compared with T-20-based lipopeptides, and this might be due to their different binding sites at NHR.

2.2.3 Addition of Ion Pairs Resulted in Very Significant Increase of Antiviral Activity of LP-40.

The present invention further attempted to promote the helical structure and antiviral activity of LP-40 by introducing ion pairs. In the present technology, the EEKK amino acid residues that contribute to the formation of a "salt bridge structure" were introduced by mutating amino acids at the non-NHR binding surface of the polypeptide sequence (i.e., the positions of b, c and f, g). As could be seen from FIG. 1, the 11 amino acids in the LP-40 polypeptide sequence were substituted by E or K, thereby three pairs of EEKK motifs were introduced at the positions of i and i+4, and the synthesized lipopeptide was named LP-50. The inhibitory activity of LP-50 was determined by the three antiviral assays, and the results were unbelievable! As shown in FIG. 2, the $IC_{50}$ values of LP-50 for inhibiting cell fusion, pseudovirus and replicative virus were 21 pM, 7 pM and 23 pM, respectively, and were as 1151 folds, 1345 folds and 226 folds as that of T-20, respectively, and as 20 folds, 63 folds and 12 folds as that of LP-40. Therefore, the introduction of ion pairs might increase the stability of the helical structure of the lipopeptide by forming a "salt bridge structure", thereby greatly increasing the antiviral activity of the lipopeptide. This was confirmed by subsequent circular dichroism assays (please see the experimental results of Example 7 below).

2.2.4 Addition of HIV-2/SIV Amino Acid Residues Further Improved the Activity of LP-50.

In order to further improve the antiviral activity of LP-50, the present invention further attempted to synthesize lipopeptides LP-51 and LP-52 by introducing corresponding amino acid residues derived from HIV-2 and/or SIV at the NHR binding surface of the polypeptide, i.e., the positions of a and d, or adjacent positions. The mutated amino acids were shown in FIG. 1. The polypeptide sequences of LP-51 and LP-52 retained only 10 original amino acid residues of the gp41 and were less than 28% identical to the sequence of T-20. The results of antiviral assays showed that the activity of the LP-51 was comparable to that of the LP-50, and the inhibitory activity of the LP-52 against HIV-1 strain HBX2-mediated cell fusion, NL4-3 pseudovirus and replicative JRCSF virus was further improved by about 2 folds, 2 folds and 5 folds, respectively. As compared to T-20, the inhibitory activity of the LP-52 against HIV activity in three assay systems was as 1859 folds, 2353 folds and 1038 folds as that of T-20, respectively. Therefore, it could be concluded that the LP-50, LP-51 and LP-52 were extremely potent HIV membrane fusion inhibitors.

2.2.5 Identification of a Core Sequence of Potent Anti-HIV Lipopeptides

The polypeptide sequence of the above potent HIV inhibitor was 28 amino acids in length. In order to identify the key sequence and the possibility to design a lipopeptide containing a shorter sequence, in the present invention, a C-terminally truncated lipopeptide LP-53 based on the LP-40 was first synthesized and a C-terminally truncated lipopeptide LP-54 based on the LP-50 was synthesized, and it was found that the antiviral ability thereof was markedly reduced (FIG. 2). Further, LP-55 and LP-56 were synthesized by using the LP-52 as a template, wherein the LP-56 contained an AEEA as a linker arm for substituting the three amino acid residues (LEK) at the C-terminus. The antiviral assays revealed that although the inhibitory activities of LP-55 and LP-56 against HXB2-cell fusion were essentially unchanged, their inhibitory activity against NL4-3 and JRCSF infection was decreased (by about 2 fold). These experimental results indicated that the three amino acid residues (LEK) at the C-terminus of the lipopeptide play an important role in the antiviral activity.

A set of N-terminally truncated lipopeptides (LP-60 to LP-68) was further synthesized. The antiviral assays revealed that the activity of two truncated lipopeptides based on LP-50, i.e., LP-60 and LP-61, was also decreased significantly; but surprisingly, the activity of the truncated lipopeptides based on LP-52, i.e., LP-62, LP-63 and LP-65, did not change largely, especially the activity of the LP-65 with only 24 amino acids was equivalent to that of the LP-52, and the activity, particularly the inhibitory activity against cell fusion, of the LP-64 containing 25 amino acids was decreased significantly. Studies had found that further N-terminal truncation resulted in a significant decrease in activity of the lipopeptides (LP-66, LP-67) or even loss of antiviral capacity thereof (LP-68). LP-69 was synthesized by truncating the C-terminal LEK on the basis of the LP-65. Although the antiviral activity of the LP-69 was significantly decreased, it still had potent inhibitory activity against the viruses as compared with a lipopeptide having only 21 amino acids. The results of these studies showed that the sequence "IEELX$_9$KKX$_{12}$EEQQKKNEEELKK" consisting of 21 amino acids was the core sequence of the potent lipopeptides of the present invention, which corresponded to the amino acid sequence at the positions of 5 to 25 of the T-20, that is, corresponding to the amino acid sequence at the positions of 131 to 151 (IHSLIEESQNQQEK-NEQELLE) of the gp41 from the HIV-1 strain HXB2. Addition of WEQK (or LEAN or YTSL) to the N-terminus of the core sequence or addition of LEK to its C-terminus could effectively increase the antiviral activity; if the amino acid motifs were retained at the both termini (e.g., LP-52), the activity of such a lipopeptide could be further improved.

The results also showed that the antiviral activity of LP-57 was decreased by about 15 to 150 folds as compared to that of LP-55, indicating that three terminal amino acids LKK of the LP-55 were important, and were not suitably be further truncated; the antiviral activity of the LP-66 was about 54 to 158 folds lower than that of the LP-65, indicating that the first amino acid (Ile) of the LP-65 was critical and was not suitably be further truncated. At the same time, the difference between the two truncated lipopeptide LP-65 and LP-61 only is one amino acid (S and A at the position of 8, respectively), but their activity differed by 5 to 9 folds, indicating that the substitution of A for S was very important for the potent lipopeptides of the present invention.

Meantime, in order to reveal the relationship between the sequence structure and function of the potent antiviral lipopeptides, in the present invention, a set of N-terminally extended lipopeptides (LP-70 to LP-75 in FIG. 2) were further designed and synthesized, wherein the LP-74 contained a pocket-binding domain (PBD) sequence, the LP-75 contained both PBD sequence and M-T hook forming sequence. Surprisingly, as the polypeptide sequence extended along the N-terminus, the antiviral activity of lipopeptides was not increased but was reduced, and in particular, the activity of the LP-74 and LP-75 was significantly reduced.

2.2.6 Derivatives of Potent Anti-HIV Lipopeptides and Antiviral Activity Thereof In order to reveal the sequence and structural specificity of potent anti-HIV lipopeptides, in the present invention, lipopeptides modified with different lipophilic compounds, including fatty acids of different chain lengths, cholesterol, dihydrosphingosine, and vitamin E, were continued to be designed and synthesized. The results of antiviral assays were shown in FIG. 2. The inhibitory activity of the stearic acid (C18)-modified LP-80 against NL4-3 entry and JRCSF replication was even greater than that of C16-modified LP-52, but the inhibitory activity of dodecanoic acid (C12)-modified LP-81 and the octanoic acid (C8)-modified LP-82 was significantly decreased. These four lipopeptides had the same polypeptide sequence, but the inhibitory activity of the lipopeptides was determined by the length of fatty acid chains. Therefore, long chain fatty acids with a chain length of C18 and C16 were more suitable for modifying the polypeptide sequence. The results of antiviral assays also demonstrated that the lipopeptides modified by cholesterol (LP-83 and LP-86), dihydrosphingosine (LP-84 and LP-87) and vitamin E (LP-85) also had strong antiviral effects. In addition, the C18-modified N-terminally truncated lipopeptides LP-88, LP-89 and LP-90 also had potent antiviral activity. Interestingly, the LP-89 with 25 amino acids was lower active than the LP-90 with 24 amino acids. This phenomenon was similar to that of C16-modified LP-64 and LP-65. Accordingly, the N-terminal lysine (K) was not necessary for a potent short lipopeptide based on the core sequence. For the core sequence of 21 amino acids, the activity of the C16- and C18-modified lipopeptides (LP-69 and LP-92) was substantially equivalent.

In the meantime, in the present invention, the antiviral activity of several control lipopeptides, including the LP-11, LP-19, C34-Chol and C34-C16, was determined (see, FIG. 2). It could be seen that the control lipopeptides could effectively inhibit HIV-1 mediated cell fusion, entry and replication, and the activity thereof was significantly higher than that of T-20, but significantly lower than that of some of the potent lipopeptides of the present invention, such as the C16-modified LP-52, LP-55 and LP-65 and C18-modified LP-80, LP-90 and LP-91 and the like.

Example 3 Inhibitory Activity of Potent HIV Membrane Fusion Inhibitors Against Different Subtypes of HIV-1

AIDS was mainly caused by HIV-1, and multiple subtypes were generated due to virus variation, including A-D, F-H, J and K subtypes, and the like. Among them, the A, B and C subtypes were the main viruses causing AIDS epidemic in the world, while B/C and A/E recombinant viruses were the main viruses in China. In order to further evaluate the activity of the potent HIV membrane fusion inhibitors, in the present invention, a group of 35 HIV-1 pseudoviruses, including international representative strains and HIV-1 strains currently epidemic in China, were prepared, wherein the strains included 3 subtype A strains, 8 subtype B strains, 4 subtype B' strains, 7 subtype C strains, 1 subtype G strain, 1 recombinant A/C strain, 5 recombinant A/E strains and 6 recombinant B/C strains. Among the Env expression plasmids used for the preparation of pseudoviral, except that the Env expression plasmids used for preparation of PVO, Du156 and CAP 210.2.00.E8 were obtained from the AIDS Reagent Program of NIH in the United states, other plasmids were preserved by the laboratory of Prof. He Yuxian, Institute of Pathogen Biology, Chinese Academy of Medical Sciences, please see the References 13, 14 and 18 listed in the Background Art and articles of Chong et al. (Chong H, Yao X, Zhang C, Cai L, Cui S, Wang Y, He Y. Biophysical property and broad anti-HIV activity of Albuvirtide, a 3-maleimimidoproprotionic acid-modified peptide fusion inhibitor. PLoS One, 2012; 7 (3): e 32599). The preparation of the pseudovirus and the antiviral assay were the same as those in Example 2.1 of Example 2 (HIV-1 pseudovirus-mediated cell entry inhibition assay). For comparison and analysis, in the present example, the inhibitory activity of 12 inhibitors, including T-20, LP-40, LP-50, LP-51, LP-52, LP-55, LP-65, LP-80, LP-85, LP-90 and control lipopeptides LP-19, C34-Chol, against the 35 pseudoviruses described above was determined. As shown in FIG. 3, the average $IC_{50}$ values of the T-20, LP-40, LP-50, LP-51, LP-52, LP-55, LP-65, LP-80, LP-85, and LP-90 for inhibition of various types of HIV-1 pseudoviruses were 41410 pM, 6369 pM, 41 pM, 33 pM, 16 pM, 34 pM, 52 pM, 6 pM, 44 pM, and 14 pM, respectively. It could be seen that the inhibitory activity of the newly synthesized lipopeptides of the present invention against different subtypes of HIV-1 was significantly higher than that of the T-20, which was as 7 folds, 1010 folds, 1255 folds, 2588 folds, 1218 folds, 796 folds, 6902 folds, 941 folds and 2958 folds as that of the T-20. Among them, the LP-80 showed the strongest inhibitory activity against the viruses, and the average $IC_{50}$ values for 35 pseudoviruses was 6 pM, and the $IC_{50}$ values for many strains were even lower than 1 pM. The average $IC_{50}$ values of the control LP-19 and C34-Chol for inhibiting various HIV-1 pseudoviruses were 439 pM and 66 pM, respectively, and the activity thereof was lower than that of the LP-50, LP-51, LP-55, LP-65 and LP-85, and was more significantly lower than that of the LP-52, LP-80 and LP-90. By comparing the $IC_{50}$ values of the LP-52 and LP-80, LP-65 and LP-90, it was revealed that the antiviral activity of the C18-modified lipopeptides was superior to that of the C16-modified lipopeptides.

Figures 4, 5:
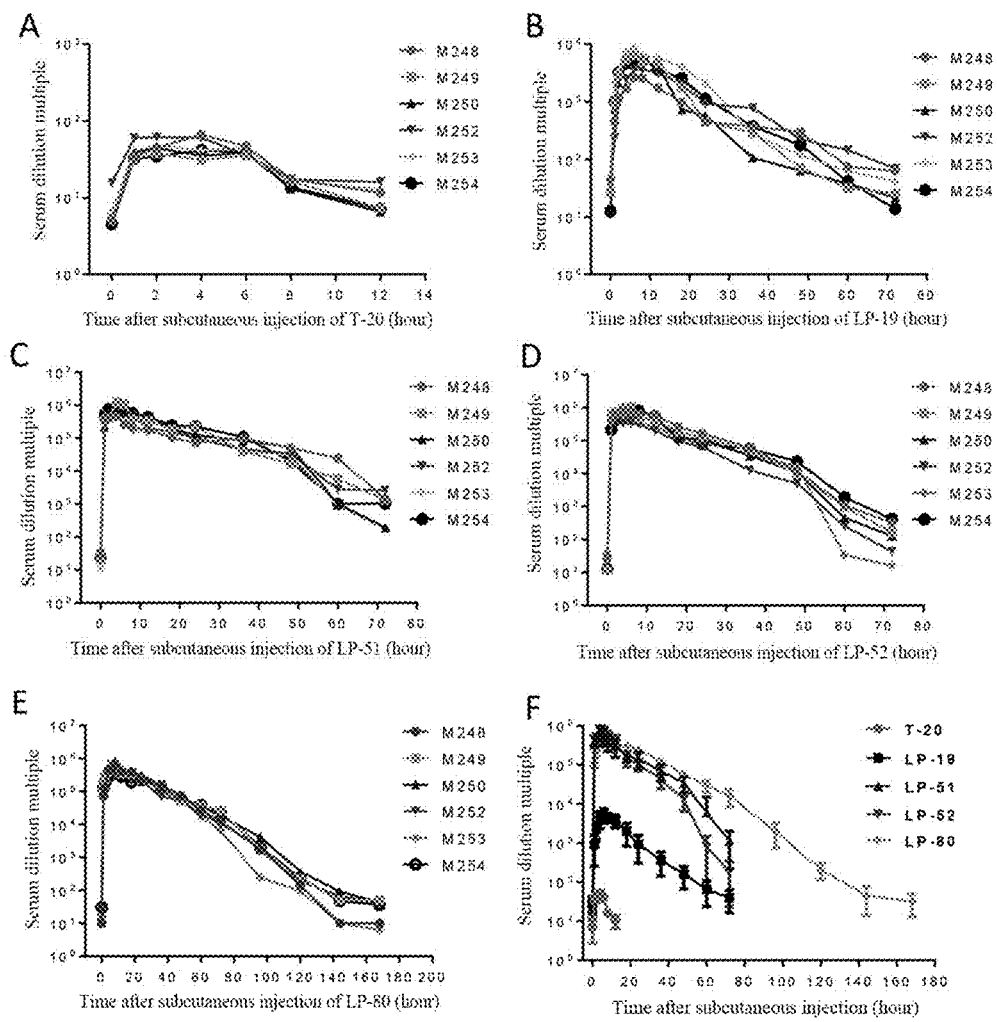
FIG. 4 shows the inhibitory effect of HIV membrane fusion inhibitors on T-20 resistant mutant strains, HIV-2 strains and SIV strains. The T-20 resistant mutant strains and the SIV strains are pseudoviruses, and the HIV-2 strains is an infectious ROD strain. The experiment is repeated three times and the average $IC_{50}$ value is calculated.
FIG. 5 shows the antiviral activity in serum of macaque after injection of HIV membrane fusion inhibitors. In the figure, M248, M249, M250, M252, M253 and M254 are the serial numbers of macaque.

Example 4 Inhibitory Activity of Potent HIV Membrane Fusion Inhibitors Against T-20-Resistant Strains T-20 is only one HIV membrane fusion inhibitor approved for clinical use at present, but its activity is not only lower than that of a new generation of polypeptides, but also it easily induces drug-resistance mutations, often leading to failure of clinical treatment. In order to fully reflect the antiviral broad spectrum and advantages of potent lipopeptides of the present invention, NL4-3 pseudovirus carrying a common T-20 resistance mutation site of NHR were prepared in this example (as shown in FIG. 4, the subscript of the strain name in FIG. 4 was the strain name in Table 2 in the Reference 14 listed in the Background Art). The methods for preparation of plasmids and pseudovirus and antiviral activity assays used were described in the literatures published by the present inventors (see the References 11, 12, 14 and 18 listed in the Background Art) and in the above Examples 2 and 3. The results were shown in FIG. 4. Compared with a representative NL4-3$_{D36G}$ mutant, the wild type NL4-3$_{WT}$ itself showed resistance to T-20, and corresponding $IC_{50}$ values thereof were 13.65 nM and 152.23 nM, respectively. However, the drug resistance of strains containing single or double mutations to T-20 was significantly increased by several folds. The results showed that the sensitivity of these T-20 resistant strains to LP-40 had been improved. From the experimental results, it could be found that the inhibitory activity of the lipopeptide LP-50 designed by introducing ion pairs on the basis of the LP-40 to form a salt bridge structure against T-20 resistant strains was further improved by hundreds or even thousands of folds. The ability of the lipopeptides LP-51, LP-52, LP-80 and LP-85 modified with the HIV-2/SIV sequence to overcome resistant strains was greatly improved, which was thousands to tens of thousands of times better than that of the LP-40. By comparing LP-52, LP-55 and LP-65, LP-80 and LP-90, it was found that: although the C-terminally truncated lipopeptide LP-55 and the N-terminally truncated lipopeptides LP-65 and LP-90, which were shown to be outstanding in the previous antiviral activity assays, had inhibitory activity against a large number of HIV-1 strains which was even comparable to that of the LP-52 and LP-80, they were much lower active against T-20 resistant mutant strains than the LP-52 and LP-80. It is worthy of particular emphasis that representative lipopeptides as potent inhibitors of the present invention, including the LP-50, LP-51, LP-52, LP-55, LP-65, LP-80, LP-85 and LP-90, had significantly reduced inhibitory ability to most T-20 resistant strains, but they still had strong antiviral activity, especially the activity of the LP-52 and LP-80 was still rare in the field. This example also revealed from one aspect that the NHR sequence of the gp41 was still a main target of the potent lipopeptides of the present invention.

Example 5 Inhibitory Activity of Potent HIV Membrane Fusion Inhibitors Against HIV-2 and SIV In order to further reflect the antiviral advantages of the potent lipopeptides of the present invention, their inhibitory activity against HIV-2 and SIV was determined in the example. The methods of antiviral activity assays used were described in the literatures published by the present inventors (see the References 13 and 30 listed in the Background Art). The molecular cloning plasmid pROD of the HIV-2 strain ROD (HIV-2$_{ROD}$) was kindly provided by Professor Nuno Taveira from the University of Lisbon, Portugal, and the plasmids expressing the SIV strain SIV$_{pbj}$ (SIV$_{PBJ}$) and SIV$_{239}$ envelope proteins (pSIVpbj-Env and pSIV239, respectively) were kindly provided by Professor Xu Jianqing from the Fudan University. The preparation of the infectious ROD was the same as that of the infectious JRCSF in the above section 2.1, and the pseudoviruses SIV$_{pbj}$ and SIV$_{239}$ were prepared by a method same as that described in the above Examples 2 and 3. The results were shown in FIG. 4, from which it could be seen that the inhibitory activity of the T-20 against HIV-2 and SIV strains was extremely weak, while the activity of LP-40 was only slightly improved. However, it was appreciated that the potent lipopeptides determined, including the LP-50, LP-51, LP-52, LP-65, LP-80, LP-85 and LP-90, had extremely potent inhibitory activity against both HIV-2 and SIV. Accordingly, the potent lipopeptides of the present invention were not only highly effective against various subtypes of HIV-1, but also highly effective against T-20 resistant strains, HIV-2 and SIV strains, and had extremely potent and broad-spectrum antiviral activity. By comparing the LP-52, LP-55 and LP-65, it was found that the truncation of the N-terminal amino acids WEQK had little effect on the inhibitory activity against HIV-2 and SIV, while the truncation of the C-terminal amino acids LEK significantly affected the activity.

Example 6 In Vivo Antiviral Activity of Potent HIV Membrane Fusion Inhibitors Recent studies had shown that lipopeptide-based HIV membrane fusion inhibitors not only had improved antiviral activity, but also exhibited stable metabolism in vivo, and therefore they had a longer half-life. In order to further demonstrate the application value and the drug-forming advantages of the potent lipopeptides of the present invention, the in vivo antiviral activity of the lipopeptides LP-51, LP-52 and LP-80 was mainly analyzed in this example, and the methods were described in the literatures published by the inventors (see the References 18 and 30 listed in the Background Art), wherein an inhibitor was injected into monkeys by subcutaneous route, blood samples at different time points were collected, and the antiviral activity of the inhibitor was measured in vitro; by the method, not only the in vivo activity of the inhibitor could be learned, but also the in vivo stability thereof was indirectly reflected. In addition to the three potent lipopeptides described above, this example included two controls, T-20 and LP-19, for comparison and analysis. The specific method was as follows: 6 experimental macaques (rhesus monkeys) were selected, half male and half female, aged 3-4 years old, weighing 3.4-4.7 kg. The T-20, LP-19, LP-51, LP-52 or LP-80 (all dissolved in sterile distilled water) was injected subcutaneously at 3 mg/kg body weight, and 0.4 ml of venous blood sample was collected before injection (0 hr) and at 1, 2, 4, 6, 8, 12, 18, 24, 36, 48, 60 and 72 hr after injection, respectively. For LP-80, in addition to the above-mentioned blood collection time points, four blood collection time points at 96, 120, 144 and 168 hours of after injection were added. The serum was separated according to a conventional method. The injection interval of each inhibitor was more than 2 weeks to ensure that there was no residue of the previous analyte. The serum activity against the HIV-1 strain NL4-3 (NL4-3$_{D36G}$) was measured according to the experimental method of the pseudovirus-based assay in the above examples. The serum was diluted by 3 folds. The experimental results were shown in FIG. 5. For the subcutaneous injection of the T-20, the inhibition peaks occurred at 2 and 4 hour after injection, wherein the maximum serum dilution multiples for inhibiting 50% of NL4-3 infectivity were 45 folds and 46 folds, respectively (A of FIG. 5); for the subcutaneous injection of the LP-19, the inhibition peaks occurred at 6 and 8 hour after injection, wherein the maximum serum dilution multiples were 5396 folds and 4720 folds, respectively (B of FIG. 5). However, it was surprisingly that: for the subcutaneous injection of the LP-51 or LP-52, inhibition peaks occurred at 4 and 6 hour after injection, the maximum serum dilution multiples were 700482 folds and 584381 folds for LP-51, respectively, and the maximum serum dilution multiples were 700802 folds and 669112 folds for the LP-52 (C and D of FIG. 5); and for the subcutaneous injection of LP-80, inhibition peaks occurred at 6 and 8 hour after injection, the maximum serum dilution multiples were 491409 folds and 537206 folds, respectively (E of FIG. 5). It could be seen that the serum inhibition peak of the potent lipopeptides could be as 11678 to 15235 folds as the serum inhibition peak of the T-20, and as 100 to 130 folds as the serum inhibition peak of the LP-19 (calculated according to the highest values). The more exciting result was in vivo long-acting effect of three lipopeptides, LP-51, LP-52 and LP-80, they had a higher serum inhibition peak even at 72 hours (3 days) after injection, respectively, the maximum serum dilution multiples of which were 1122, 182 and 16157 folds, respectively. In particular, the serum inhibition peak of LP-80 was maintained at 1980 folds at 96 hours (4 days) after injection, at 211 folds at 120 hours (5 days) after injection, and at 144 hours (6 days) after injection, and the serum inhibition peak thereof was same as that of the T-20 at 4 hours (46 folds) (F of FIG. 5). Therefore, the lipopeptides of the present invention were not only potent but also were long-lasting effective.

Example 7 Interaction of Potent HIV Membrane Fusion Inhibitors with NHR Target Sequences In order to investigate the mechanism of action of the potent anti-HIV lipopeptides, a circular dichroism (CD) analysis was used to determine the interaction between the inhibitors and NHR target sequences, including the secondary structure (α-helix) and helix stability (T$_m$) of the complexes formed. The circular dichroism spectrophotometer was Jasco-815 by JASCO Inc., and the assay method was referred to the papers published by the inventors (see the References 18 and 30 listed in the Background Art). The target sequence polypeptide derived from NHR was N39 (see FIG. 1) and its sequence was Ac-STMGAASMTLTVQARQLLSGIVQQQNNLL-RAIEAQQHLL-NH$_2$, which corresponded to the target site on NHR to which the T-20 bound. The N39 and an inhibitor were separately dissolved in a phosphate buffered saline (PBS) to prepare a PBS solution (pH 7.2) of a concentration of 20 μM. The N39 was mixed with an inhibitor at a volume ratio of 1:1 (final concentration of 10 μM for each), the mixed sample was placed at 37° C. for 30 minutes to fully react, and then the helix content and T$_m$ value of the resultant complex were measured by the circular dichroism spectrophotometer. The scan wavelength range of the device was 195-260 nm with a wavelength interval of 1 nm, and the values measured by scanning for three times were averaged. Based on the CD signals, the interaction between the polypeptides and the helix content were determined. Then, the sample for CD signal measurement was transferred to the temperature scanning sample cell, the program of the CD device was set to temperature scanning with a detection wavelength of 220 nm and scanning range of 20-98° C., and the program scan was performed to obtain the curve of the CD signals vs temperature, based on which the T$_m$ value was calculated. Based on the T$_m$ value, the stability of the formed helical structure of the inhibitor and N39 was judged.

Figure 7:
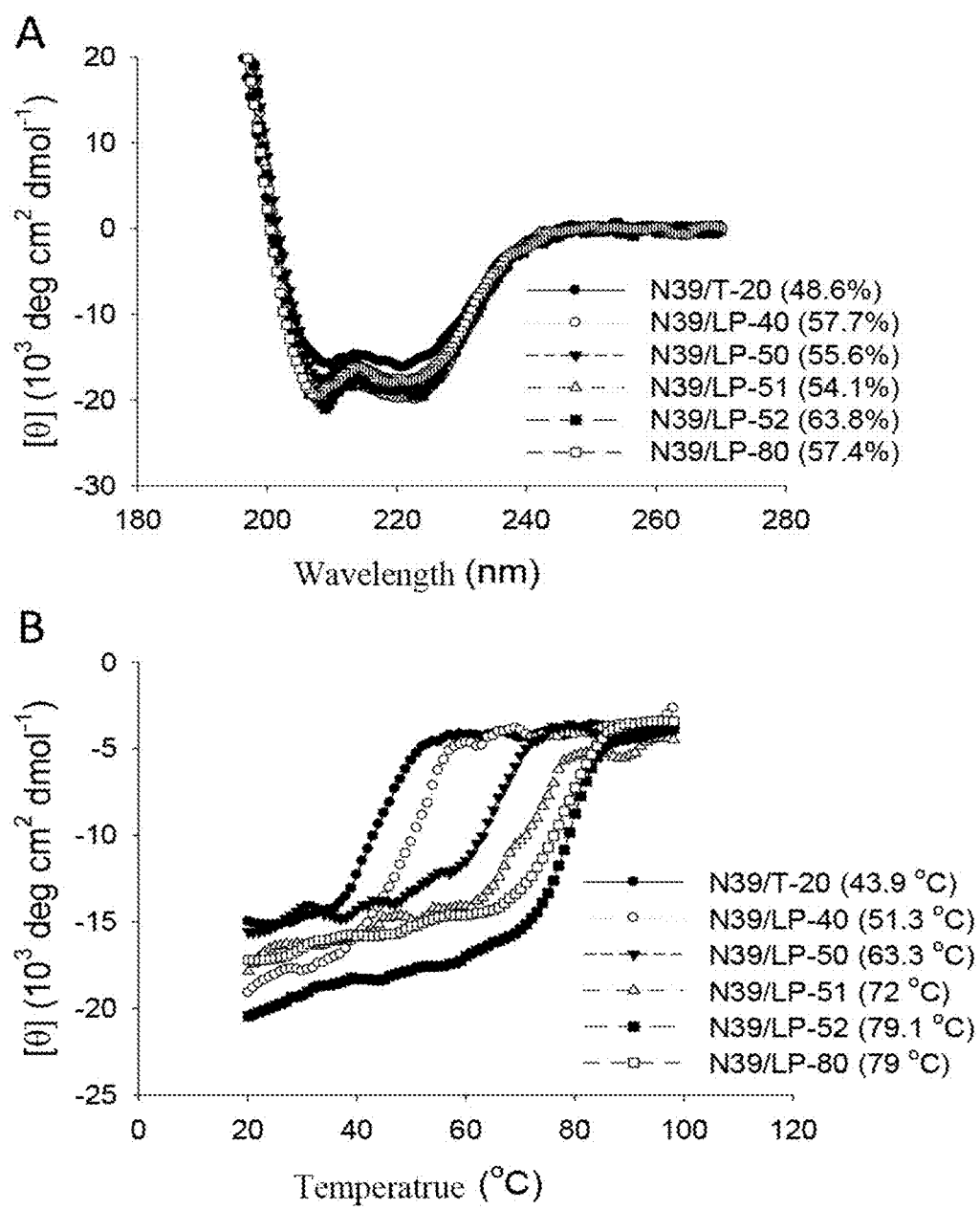
FIG. 7 shows the results of circular dichroism analysis of the interaction between NHR and T-20 or representative lipopeptides.

The results of CD assay were shown in FIG. 6. It could be seen that the T-20 could interact with the N39, and the resultant complex had a helix content of 48.6% and a T$_m$ value of 43.9° C.; however, the interaction between the T20-TRM and the N39 was extremely weak, and thus the T$_m$ value was undetectable by the device, further demonstrating the important role of the TRM in the T-20. The interaction between the lipopeptide LP-40 and the N39 was significantly enhanced, and the resultant complex had a helix content of 57.7% and a T$_m$ value of 51.3° C. The addition of a linker arm resulted in a decrease in the helix content, but most of linker arms had little effect on T$_m$ value, and only the LP-45 with the longest linker arm (PEG12) had a significantly reduced T$_m$ value. Surprisingly, the introduction of the EE**KK ion pair greatly enhanced the binding stability of the lipopeptides, which was reflected by that the T$_m$ value of the LP-50/N39 complex was increased to 63.3° C.; and the addition of the HIV-2/SIV amino acids could further enhance the binding ability of the lipopeptides, and the T$_m$ values of the LP-51/N39 and LP-52/N39 complexes were 72° C. and 79.1° C., respectively, which were significantly increased as compared to the T$_m$ values of the T-20 and LP-40 complexes, as shown in FIG. 7. Accordingly, the three potent antiviral lipopeptides were capable of forming an extremely stable helical structure with the target sequence, particularly the LP-52. Moreover, the LP-52/N39 complex also had the highest helix content (63.8%).

In this example, it was found that the C-terminal or N-terminal truncation of lipopeptides could affect their binding ability of the lipopeptides to varying extents, and some of the lipopeptides showed a reduction in T$_m$ value, and some exhibited a reduction in both helix content and T$_m$ value. The T$_m$ value of the C-terminally truncated lipopeptides (LP-53 to LP-59) was reduced significantly, indicating the important role of the three amino acids (LEK) at the C-terminus in the binding of lipopeptides to NHR. It was worth noting that the T$_m$ values of the LP-55 and LP-56 with potent antiviral activity were also decreased significantly (from 79.1 to 63.1° C.), but the T$_m$ vales were much higher than those of the LP-53, LP-54, LP-57, LP-58 and LP-59. In particular, the T$_m$ values of the LP-58 and LP-59 could not be determined due to the lower helix content. The T$_m$ values of the N-terminal truncated lipopeptides (LP-60 to LP-68) were also reduced significantly. The N-terminal truncation based on the LP-52 did affect the binding stability of the lipopeptides (LP-62 to LP-65), but the T$_m$ values of the corresponding complexes were still greater than 70° C., indicating that the lipopeptides still had a strong binding ability, and this might be the reason why they retained strong antiviral capabilities. It was worth noting that the lipopeptide LP-65 which had a sequence of 24 amino acids also had a higher helix content (63%) and T$_m$ value (72.1° C.), while further truncation severely affected the binding capacity of corresponding lipopeptides, such as the LP-66, LP-67 and LP-68, which was consistent with the antiviral activity thereof. In comparison, the effect of removal of the 3 amino acids (LEK) at the C-terminus on the binding stability (T$_m$ value) was more significant than the effect of the removal of the 1-4 amino acids (WEQK) at the N-terminus, indicating that the C-terminus of the lipopeptides played a more important role in the binding to a target. However, the core sequence lipopeptide LP-69 with the removal of amino acids at both the C-terminus and N-terminus had a significantly reduced binding stability and a T$_m$ value of 51° C. which was lower than that of the LP-52 by 28.1° C.

Another interesting phenomenon was that the N-terminally extended lipopeptides had an increased T$_m$ value, such as the performance of the LP-70 to LP-75, which was inconsistent with the reduced antiviral activity thereof. It should be noted that the LP-74 and LP-75 contained the NHR pocket-binding domain (PBD) and the M-T hook motif, which made it impossible to match N39 perfectly.

The results of the example also showed that the stearic acid (C18)-modified lipopeptide LP-80 also had a strong binding stability to N39 (T$_m$ value=79° C.). However, the lipopeptides modified with a short chain length fatty acid, e.g., the LP-81 modified with a C12 fatty acid and the LP-82 modified with a C8 fatty acid, had a significantly reduced helix content and binding capacity, the T$_m$ values thereof were 74.1° C. and 65.1° C., respectively, and their antiviral activity was decreased more significantly (see FIG. 2). The cholesterol-modified lipopeptides LP-83 and LP-86, vitamin E-modified lipopeptide LP-85, dihydrosphingosine-modified lipopeptides LP-84 and LP-87 all had a strong helical binding stability, which was consistent with their antiviral activity. Similarly, the N-terminally truncated lipopeptides based on LP-80 (LP-88, LP-89, LP-90) also had a strong binding capacity and a T$_m$ value of 76.5° C., 70° C. and 71.1° C., respectively. However, the lipopeptide LP-91 with the removal of the C-terminal LEK and the core sequence lipopeptide LP-92 with truncation at both termini had a significantly reduced helix stability, and a T$_m$ value of 61° C. and 55.1° C., respectively.

This example revealed the correlation between the sequence structure, binding stability and antiviral activity of the inhibitors by a large number of experimental results, and provided important information for understanding the mechanism of action of the potent lipopeptides of the present invention. Although the binding ability of certain inhibitors was sometimes insufficiently consistent with the antiviral activity thereof, in general, the potent lipopeptides of the present invention had extremely high T$_m$ values. This example also demonstrated that the antiviral activity of such lipopeptides was dependent on polypeptide sequences thereof and also on the properties of lipophilic compounds.

Example 8 Secondary Structure Analysis of Potent HIV Membrane Fusion Inhibitors

Figure 8:
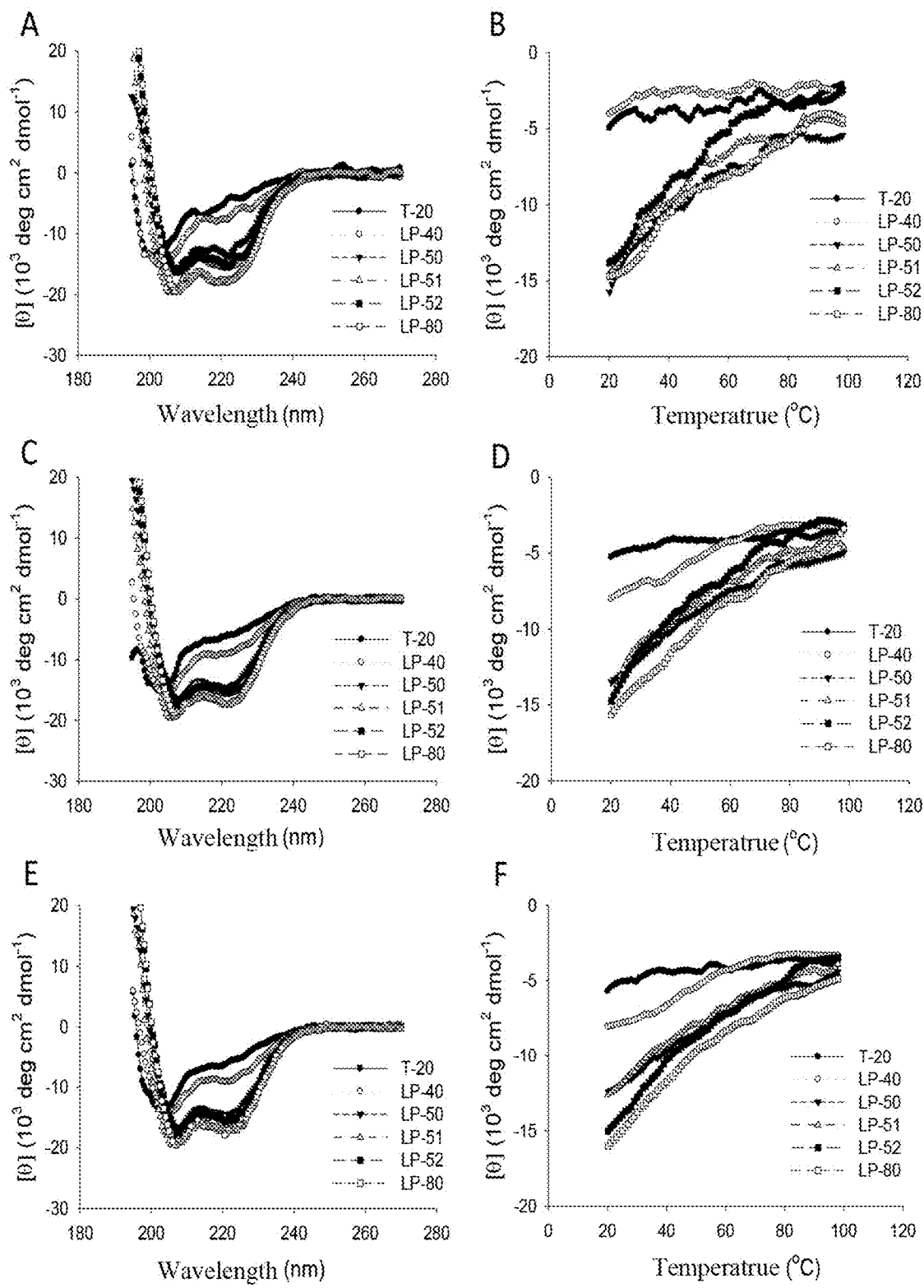
FIG. 8 shows the results of secondary structure analysis of T-20 and representative lipopeptides themselves.

In order to investigate the mechanism of action of the potent anti-HIV lipopeptides, a circular dichroism (CD) analysis was used to analyze the secondary structural characteristics of the T-20 and representative lipopeptides in solution by a manner that was same as that in Example 7. For easy analysis, the α-helix content and the $T_m$ value of the inhibitors were measured at concentrations of 10 μM, 20 μM, and 40 μM (PBS solution), respectively. The results were shown in FIG. 8. The T-20 exhibited an irregular disorder structure at three concentrations, the LP-40 exhibited a small amount of helical structure at 20 μM and 40 μM, and the four potent lipopeptides (LP-50, LP-51, LP-52, LP-80) exhibited a distinct helical structure, among which the LP-80 had the higher helix content and $T_m$ value. Therefore, the potent lipopeptides of the present invention themselves could form a typical helical structure, which was significantly different from T-20.

Example 9 Pharmacokinetic Analysis of Potent Lipopeptide LP-80 in Rats

Figure 9:
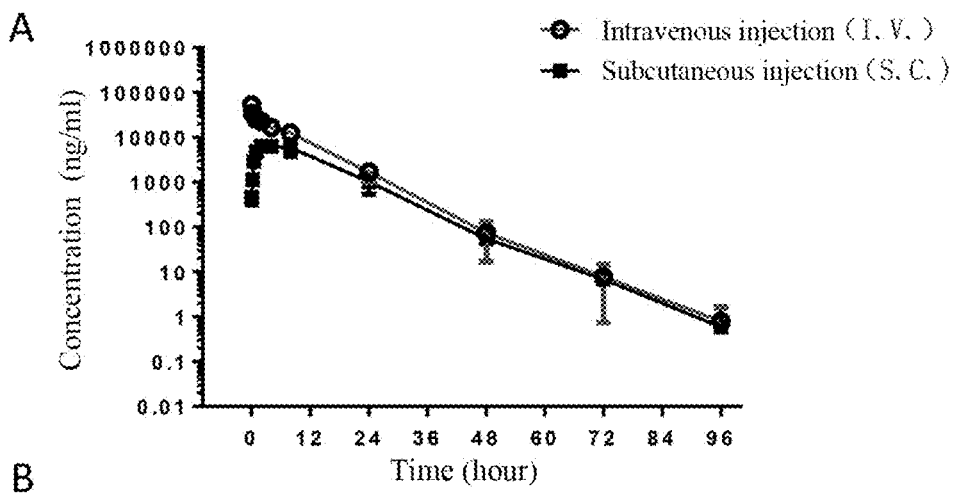
FIG. 9 shows the results of pharmacokinetics analysis of LP-80 in rats.

The above research results showed that that the LP-80 was a lipopeptide having a higher in vivo antiviral activity and was very stable among the potent lipopeptides of the present invention. In this example, the LP-80 was used as a representative to analyze its pharmacokinetic characteristics in SD rats. 12 SD rats, aged 5-8 weeks, weighing 182-219 grams, were used in test, and divided into intravenous group and subcutaneous injection group, each group of 6 animals, half male and half female. The dose of the LP-80 was 6 mg/kg body weight (mg/kg), and the LP-80 was dissolved in sterile distilled water. For the animals in each group, the serum samples were collected at time before administration and at 5 minutes, 15 minutes, 30 minutes, 1 hour, 2 hours, 4 hours, 8 hours, 24 hours, 48 hours, 72 hours, 96 hours, 120 hours, 168 hours and 216 hours after administration. The concentration of the LP-80 in rat serum was quantitatively determined by a liquid chromatography-mass spectrometry (LC-MS/MS), and the lower limit was quantified as 1 ng/ml (ng/ml). The pharmacokinetic parameters were calculated using a non-compartmental analysis model (NCA). The experimental results were as shown in FIG. 9. The average terminal half-life ($T_{1/2}$) of the LP-80 in intravenous group and the subcutaneous injection group was 6.04 hours and 6.28 hours, respectively. However, it was worth noting that the concentration of the LP-80 in serum at 3 days (72 hours) after intravenous and subcutaneous injection was 7.75 ng/ml and 6.86 ng/ml, respectively, i.e., a molar concentration of 2021.12 pM and 1789.02 pM, and the concentration was as 1010.56 folds and 894.51 folds as the $IC_{50}$ value (2 pM) of the LP-80 for inhibiting HIV-1 strains NL4-3 and JRCSF, respectively. This result further confirmed the potent and long-lasting antiviral ability of the LP-80 in the above Example 6 in the macaques from the viewpoint of pharmacokinetics.

Example 10 Evaluation of Therapeutic Effect of Potent Lipopeptides LP-80 in Monkey AIDS Model In the example, the therapeutic effect of the LP-80 on HIV infection model in monkeys was further investigated, and as to the technical route, please refer to the method used by the inventors to evaluate the LP-19 (i.e., the Reference 30 listed in the Background Art). Six adult Chinese rhesus monkeys (numbered A to F, half male and half female) were used in the test, and antibodies to SIV, herpesvirus B, and simian T-lymphotropic virus were determined to be negative. The SHIV strain SF162P3 was provided by the AIDS Reagent Program of NIH in the United States, and was amplified on peripheral blood mononuclear cells (PBMC) of the monkeys, and the $TCID_{50}$ was determined. Monkeys were intravenously inoculated with 1,000 $TCID_{50}$ of the SF162P3 virus, and changes in plasma viral load (RNA copy number/ml) in the monkeys were measured periodically. On the $197^{th}$ day after monkeys were infected with the SF162P3, the LP-80 (dissolved in sterile distilled water) was administered via subcutaneous route, and the LP-80 was administered at 2 mg per kilogram of body weight (2 mg/kg), once a day for 2 weeks, and then once per 4 days for 4 weeks. The plasma samples were isolated from monkey bloods collected at predetermined time points and the plasma viral load (RNA copy number/ml) was determined by quantitative real-time reverse transcription-polymerase chain reaction (qRT-PCR). The plasma RNA was extracted by a conventional method and cDNA samples were synthesized by reverse transcription reaction. The PCR primers were directed to the gag477 of SIV (the upstream primer was GCAGAGGAGGAAATTACCCAGTAC, the downstream primer was CAATTTTACCCAGGCATTTAATGTT, and the detection probe was FAM-ACCTGCCAT-TAAGCCCGA-MGB). The PCR device used was PE AB17500. The sensitivity of the assay was 100 RNA copies per milliliter of plasma sample.

Figure 10:
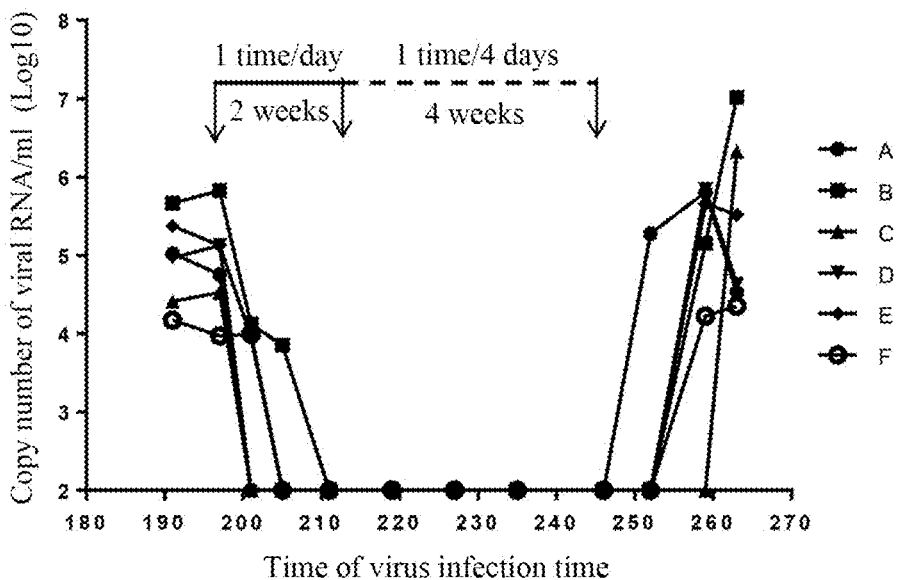
FIG. 10 shows the therapeutic effect of LP-80 in a monkey infection model.

The experimental results were as shown in FIG. 10. The viral load in three of the six monkeys on the fourth day after the treatment was decreased below the detectable level line; the viral load in five monkeys was not detected on the eighth day after the treatment; and the viral load in all six monkeys was not detected on the $14^{th}$ after the treatment. The viral load in all monkeys were controlled below the detectable level line during the subsequent treatment with administration of drug once per 4 days. The virus did not rebound on the $4^{th}$ day after the administration of the drug was stopped; there was a rebound of virus in one of the monkeys (monkey A) on the $10^{th}$ day after the administration of the drug was stopped; there was a rebound of virus in the other 5 monkeys except the monkey C on the $17^{th}$ day after the administration of the drug was stopped; and there was a rebound of viral load in all monkeys on the $24^{th}$ day after the administration of the drug was stopped. The results demonstrated the powerful antiviral therapeutic effect of the LP-80.

INDUSTRIAL APPLICABILITY

The potent lipopeptides, derivatives thereof, or pharmaceutically acceptable salts thereof, the multimers, the compositions or the pharmaceutical compounds provided by the present invention can be used for treating and/or preventing HIV (HIV-1 and/or HIV-2) and/or SIV infections. In practical applications, the lipopeptides, derivatives thereof, or pharmaceutically acceptable salts thereof, the multimers, the compositions or the pharmaceutical compounds according to the present invention can be directly administered as a drug to a patient, or mixed with a suitable carrier or excipient and administered to a patient, for the purpose of treating and/or preventing HIV infection.

The invention claimed is:

1. A lipopeptide or a pharmaceutically acceptable salt thereof, wherein the lipopeptide is the following a) or b):
   a) a lipopeptide formed by linking a polypeptide having an antiviral activity to a lipophilic compound linked to the carboxyl-terminus of the polypeptide;
   b) a lipopeptide formed by linking a polypeptide having an antiviral activity to a terminal protecting group and a lipophilic compound linked to the carboxyl-terminus of the polypeptide, wherein the terminal protecting group is an amino terminal protecting group and/or a carboxyl terminal protecting group;
   in the a) and b), the polypeptide is any one of P1 to P4:
   the P1 has a sequence as shown in the following sequence, $X_1X_2X_3X_4$IEELX$_9$KKX$_{12}$EEQQKKNEEELKKLEK;

the P2 is P2-1, P2-2, P2-3 or P2-4, wherein
   the P2-1 has a sequence as shown in the following sequence:

$X_2X_3X_4$IEELX$_9$KKX$_{12}$EEQQKKNEEELKKLEK;

the P2-2 has a sequence as shown in the following sequence:

$X_3X_4$IEELX$_9$KKX$_{12}$EEQQKKNEEELKKLEK;

the P2-3 has a sequence as shown in the following sequence:

$X_4$IEELX$_9$KKX$_{12}$EEQQKKNEEELKKLEK;

the P2-4 has a sequence as shown in the following sequence:

IEELX$_9$KKX$_{12}$EEQQKKNEEELKKLEK;

the P3 has a sequence as shown in the following sequence:

$X_1X_2X_3X_4$IEELX$_9$KKX$_{12}$EEQQKKNEEELKK;

the P4 has a sequence as shown in the following sequence:

$X_1X_2X_3X_4$IEELX$_9$KKX$_{12}$EEQQKKNEEELKKLEKC;

wherein $X_1$ is W, L or Y, $X_2$ is E or T, $X_3$ is Q, A or S, $X_4$ is K, N or L, $X_9$ is L or I, $X_{12}$ is A or S; and
   the lipophilic compound is a fatty acid containing 8 to 20 carbon atoms, cholesterol, dihydrosphingosine or vitamin E.

2. The lipopeptide or a pharmaceutically acceptable salt thereof according to claim 1, wherein
   the P1 is P-80/84/85/52, P-87/51 or P50, wherein the P-80/84/85/52 is a polypeptide represented by the sequence of SEQ ID NO: 1 in the sequence listing, the P-87/51 is a polypeptide represented by the sequence of SEQ ID NO: 2 in the sequence listing, and the P50 is a polypeptide represented by the sequence of SEQ ID NO: 3 in the sequence listing;
   the P2-1 is P-88/62, wherein the P-88/62 is a polypeptide represented by the sequence of SEQ ID NO: 4 in the sequence listing;
   the P2-2 is P63 or P60, wherein the P63 is a polypeptide represented by the sequence of SEQ ID NO: 5 in the sequence listing, and the P60 is a polypeptide represented by the sequence of SEQ ID NO: 6 in the sequence listing;

the P2-3 is P-89/64, wherein the P-89/64 is a polypeptide represented by the sequence of SEQ ID NO: 7 in the sequence listing;

the P2-4 is P-90/65 or P61, wherein the P-90/65 is a polypeptide represented by the sequence of SEQ ID NO: 8 in the sequence listing; and the P61 a polypeptide represented by the sequence of SEQ ID NO: 9 in the sequence listing;

the P3 is P-91/55, wherein the P-91/55 is a polypeptide represented by the sequence of SEQ ID NO: 10 in the sequence listing; and the P4 is a P83 or P86, wherein the P83 is a polypeptide represented by the sequence of SEQ ID NO: 11 in the sequence listing, and the P86 is a polypeptide represented by the sequence of SEQ ID NO: 12 in the sequence listing.

3. The lipopeptide or a pharmaceutically acceptable salt thereof according to claim 1, wherein the fatty acid containing 8 to 20 carbon atoms is stearic acid or palmitic acid.

4. The lipopeptide or a pharmaceutically acceptable salt thereof according to claim 3, wherein the lipopeptide is any one of the following 12 lipopeptides LP-80/84/85/52, LP-90/65, LP-87/51, LP-88/62, LP-50, LP-83, LP-91/55, LP-86, LP-63, LP-89/64, LP-60 and LP-61;

the LP-80/84/85/52 is LP-80/84/85/52a or LP-80/84/85/52b, wherein the LP-80/84/85/52a is formed by linking a polypeptide named as P-80/84/85/52 to a lipophilic compound linked to the carboxyl-terminus of the P-80/84/85/52; the LP-80/84/85/52b is formed by linking the LP-80/84/85/52a to the terminal-protecting group; in the LP-80/84/85/52a and LP-80/84/85/52b, the P-80/84/85/52 is the polypeptide represented by the sequence of SEQ ID NO: 1 in the sequence listing, and the lipophilic compound is stearic acid, dihydrosphingosine, or vitamin E;

the LP-90/65 is LP-90/65a or LP-90/65b, wherein the LP-90/65a is formed by linking a polypeptide named as P-90/65 to a lipophilic compound linked to the carboxyl-terminus of the P-90/65; the LP-90/65b is formed by linking the LP-90/65a to the terminal protecting group; in the LP-90/65a and LP-90/65b, the P-90/65 is a polypeptide represented by the sequence of SEQ ID NO: 8 in the sequence listing, and the lipophilic compound is stearic acid or palmitic acid;

the LP-87/51 is LP-87/51a or LP-87/51b, wherein the LP-87/51a is formed by linking a polypeptide named as P-87/51 to a lipophilic compound linked to the carboxyl-terminus of the P-87/51; the LP-87/51b is formed by linking the LP-87/51a to the terminal protecting group; in the LP-87/51a and LP-87/51b, the P-87/51 is a polypeptide represented by the sequence of SEQ ID NO: 2 in the sequence listing, and the lipophilic compound is dihydrosphingosine or palmitic acid;

the LP-88/62 is LP-88/62a or LP-88/62b, wherein the LP-88/62a is formed by linking a polypeptide named as P-88/62 to a lipophilic compound linked to the carboxyl-terminus of the P-88/62; the LP-88/62b is formed by linking the LP-88/62a to the terminal protecting group; in the LP-88/62a and LP-88/62b, the P-88/62 is a polypeptide represented by the sequence of SEQ ID NO: 4, and the lipophilic compound is stearic acid or palmitic acid;

the LP-50 is LP-50a or LP-50b, wherein the LP-50a is formed by linking a polypeptide named as P50 to palmitic acid linked to the carboxyl-terminus of the P50; the LP-50b is formed by linking the LP-50a to the terminal protecting group; in the LP-50a and LP-50b, the P50 is a polypeptide represented by the sequence of SEQ ID NO: 3 in the sequence listing;

the LP-83 is LP-83a or LP-83b, wherein the LP-83a is formed by linking a polypeptide named as P83 to cholesterol linked to the carboxyl-terminus of the P83; the LP-83b is formed by linking the LP-83a to the terminal protecting group; in the LP-83a and LP-83b, the P83 is a polypeptide represented by the sequence of SEQ ID NO: 11 in the sequence listing;

the LP-91/55 is LP-91/55a or LP-91/55b, wherein the LP-91/55a is formed by linking a polypeptide named as P-91/55 to a lipophilic compound linked to the carboxyl-terminus of the P-91/55; the LP-91/55b is formed by linking the LP-91/55a to the terminal protecting group; in the LP-91/55a and LP-91/55b, the P-91/55 is a polypeptide represented by the sequence of SEQ ID NO: 10, and the lipophilic compound is stearic acid or palmitic acid;

the LP-86 is LP-86a or LP-86b, wherein the LP-86a is formed by linking a polypeptide named as P86 to cholesterol linked to the carboxyl-terminus of the P86; the LP-86b is formed by linking the LP-86a to the terminal protecting group; in the LP-86a and LP-86b, the P86 is a polypeptide represented by the sequence of SEQ ID NO: 12 in the sequence listing;

the LP-63 is LP-63a or LP-63b, wherein the LP-63a is formed by linking a polypeptide named as P63 to palmitic acid linked to the carboxyl-terminus of the P63; the LP-63b is formed by linking the LP-63a to the terminal protecting group; in the LP-63a and LP-63b, the P63 is a polypeptide represented by the sequence of SEQ ID NO: 5 in the sequence listing;

the LP-89/64 is LP-89/64a or LP-89/64b, wherein the LP-89/64a is formed by linking a polypeptide named as P-89/64 to a lipophilic compound linked to the carboxyl-terminus of the P-89/64; the LP-89/64b is formed by linking the LP-89/64a to the terminal protecting group; in the LP-89/64a and LP-89/64b, the P-89/64 is a polypeptide represented by the sequence of SEQ ID NO: 7 in the sequence listing, and the lipophilic compound is stearic acid or palmitic acid;

the LP-60 is LP-60a or LP-60b, wherein the LP-60a is formed by linking a polypeptide named as P60 to palmitic acid linked to the carboxyl-terminus of the P60; the LP-60b is formed by linking the LP-60a to the terminal protecting group; in the LP-60a and LP-60b, the P60 is a polypeptide represented by the sequence of SEQ ID NO: 6 in the sequence listing; and the LP-61 is LP-61a or LP-61b, wherein the LP-61a is formed by linking a polypeptide named as P61 to palmitic acid linked to the carboxyl-terminus of the P61; the LP-61b is formed by linking the LP-61a to the terminal protecting group; in the LP-61a and LP-61b, the P61 is a polypeptide represented by the sequence of SEQ ID NO: 9 in the sequence listing.

5. A multimer
formed by the lipopeptide or a pharmaceutically acceptable salt thereof according to claim 1.

6. A composition comprising C1) and C2), wherein,
the C1) is C11), wherein the C11) is the lipopeptide or a pharmaceutically acceptable salt thereof according to claim 1;

the C2) is a pharmaceutically acceptable carrier or adjuvant;
the composition has at least one function of the following functions F1)-F5):
F1) having activity against virus;
F2) treating and/or preventing and/or adjunctively treating a disease caused by a virus infection;
F3) inhibiting fusion of virus and cell;
F4) inhibiting entry of virus into cell; and
F5) inhibiting replication of virus;
in the F1)-F5), the virus is any one virus selected from the group consisting of the following v1-v7:
v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

7. A method of treating or/and preventing an infection caused by a virus in an animal, comprising administering to a subject animal the C11) to inhibit viral infection in the animal, wherein
the C11) is the lipopeptide or a pharmaceutically acceptable salt thereof according to claim 1;
the virus is any one virus selected from the group consisting of the following v1-v7:
v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

8. A composition comprising C1) and C2), wherein,
the C1) is C13), wherein the C13) is the multimer according to claim 5;
the C2) is a pharmaceutically acceptable carrier or adjuvant;
the composition has at least one function of the following functions F1)-F5):
F1) having activity against virus;
F2) treating and/or preventing and/or adjunctively treating a disease caused by a virus infection;
F3) inhibiting fusion of virus and cell;
F4) inhibiting entry of virus into cell; and
F5) inhibiting replication of virus;
in the F1)-F5), the virus is any one virus selected from the group consisting of the following v1-v7:
v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

9. A method of treating or/and preventing an infection caused by a virus in an animal, comprising administering to a subject animal the C13) to inhibit viral infection in the animal, wherein
the C13) is the multimer according to claim 5;
the virus is any one virus selected from the group consisting of the following v1-v7:
v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

10. A method of treating or/and preventing an infection caused by a virus in an animal, comprising administering to a subject animal the C14) to inhibit viral infection in the animal, wherein
the C14) is the composition according to claim 6;
the virus is any one virus selected from the group consisting of the following v1-v7:
v1: HIV-1, HIV-2 and SIV;
v2: HIV-1 and HIV-2;
v3: HIV-1 and SIV;
v4: HIV-2 and SIV;
v5: HIV-1;
v6: HIV-2; and
v7: SIV.

* * * * *